(12) United States Patent
Treado et al.

(10) Patent No.: US 7,945,393 B2
(45) Date of Patent: *May 17, 2011

(54) DETECTION OF PATHOGENIC MICROORGANISMS USING FUSED SENSOR DATA

(75) Inventors: Patrick J Treado, Pittsburgh, PA (US); Robert C Schweitzer, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/339,805

(22) Filed: Dec. 19, 2008

(65) Prior Publication Data

US 2009/0163369 A1 Jun. 25, 2009

Related U.S. Application Data

(63) Continuation-in-part of application No. 11/450,138, filed on Jun. 9, 2006, and a continuation-in-part of application No. 12/191,496, filed on Aug. 14, 2008, now Pat. No. 7,623,232, and a continuation of application No. 11/206,007, filed on Aug. 17, 2005, now Pat. No. 7,428,045, which is a continuation-in-part of application No. 10/922,006, filed on Aug. 18, 2004, now Pat. No. 6,950,184, which is a continuation-in-part of application No. 10/823,902, filed on Apr. 14, 2004, now Pat. No. 6,917,423, which is a continuation of application No. 10/339,807, filed on Jan. 10, 2003, now Pat. No. 6,765,668.

(60) Provisional application No. 61/015,532, filed on Dec. 20, 2007, provisional application No. 60/688,812, filed on Jun. 9, 2005, provisional application No. 60/711,593, filed on Aug. 26, 2005, provisional application No. 60/347,806, filed on Jan. 10, 2002.

(51) Int. Cl.
*G01N 33/48* (2006.01)
*G01N 33/50* (2006.01)

(52) U.S. Cl. .......... 702/19; 702/181; 707/749; 436/161; 436/173; 356/301

(58) Field of Classification Search .................. None
See application file for complete search history.

(56) References Cited

U.S. PATENT DOCUMENTS

| | | | |
|---|---|---|---|
| 5,446,681 A | 8/1995 | Gethner et al. | |
| 6,553,334 B2 | 4/2003 | Gross et al. | |
| 6,609,086 B1 | 8/2003 | Bao et al. | |
| 6,765,668 B2 | 7/2004 | Gardner et al. | |
| 6,917,423 B2 | 7/2005 | Gardner et al. | |
| 6,950,184 B2 | 9/2005 | Stewart et al. | |
| 7,428,045 B2 | 9/2008 | Stewart et al. | |
| 7,623,232 B2 | 11/2009 | Stewart et al. | |
| 2002/0183602 A1 | 12/2002 | Wenzel et al. | |
| 2004/0073120 A1 | 4/2004 | Motz et al. | |
| 2004/0143402 A1 | 7/2004 | Colinge et al. | |
| 2004/0162685 A1 | 8/2004 | Gross et al. | |
| 2005/0065732 A1 | 3/2005 | Tilton et al. | |
| 2005/0143936 A1 | 6/2005 | Laughlin et al. | |
| 2007/0192035 A1 | 8/2007 | Schweitzer et al. | |
| 2008/0300826 A1 | 12/2008 | Schweitzer et al. | |
| 2009/0163369 A1 | 6/2009 | Treado et al. | |

FOREIGN PATENT DOCUMENTS

| | | |
|---|---|---|
| WO | 2004038602 | 5/2004 |
| WO | WO/2006/135806 A2 | 12/2006 |

OTHER PUBLICATIONS

Osamu Yamamoto et al, An Integrated Spectral Data Base System Including IR, MS, 1H-NMR, 13C-NMR, ESR and Raman Spectra, Analytical Sciences [online], vol. 4, Jun. 1998, pp. 233-239, XP002534313.

Masui H et al, Spectra: A Spectral Information Management System Featuring A Novel Combined Search Function, Journal of Chemical Information and Computer Sciences ACS USA, vol. 36, No. 2, Mar. 1996 pp. 294-298. XP002534314.

K. Tanabe et al, Cosmos-Combined Search System for Molecular Spectra, Computer Enhanced Spectroscopy, vol. 2, No. 3, 1984, pp. 97-99, XP008108808, vol. 2, No. 3, Jul. 2000, pp. 1-7, XP008107468.

Dennis Ward, Use of X-Ray Spectral Database in Forensic Science, Forensic Science Communication [online], vol. 2, No. 3, Jul. 2000, pp. 1-7, XP0081087468.

David Sparkman, Evaluating Electron Ionization Mass Spectral Library Search Results, Elsevier Science Inc, US vol. 7, No. 4, Apr. 1, 1996, pp. 313-318. XP, 004720392.

Schweitzer, et al., "The Role of Chemometrics in Chemical Image Analysis", North American Chapter of International Chemometrics Society, Newsletter #21, Oct. 2000, pp. 14-21.

*Primary Examiner* — Carolyn L. Smith
(74) *Attorney, Agent, or Firm* — Kristin Biedinger, Esq.

(57) ABSTRACT

A system and method to search spectral databases to identify unknown materials, specifically pathogenic microorganisms. A library is provided, having sublibraries containing reference data sets of known materials and test data sets, both generated by at least one spectroscopic data generating instrument. For each test data set, each sublibrary associated with the instrument used is searched. A set of scores for each searched sublibrary is produced, representing the likelihood of a match between the reference data set and test data set. Relative probability values are calculated for each searched sublibrary. All relative probability values are fused producing a set of final probability values, used in determining whether the unknown material is represented through a known material in the library. The known material represented in the libraries having the highest final probability value is reported, if the highest final probability value is greater than or equal to the minimum confidence value.

29 Claims, 13 Drawing Sheets

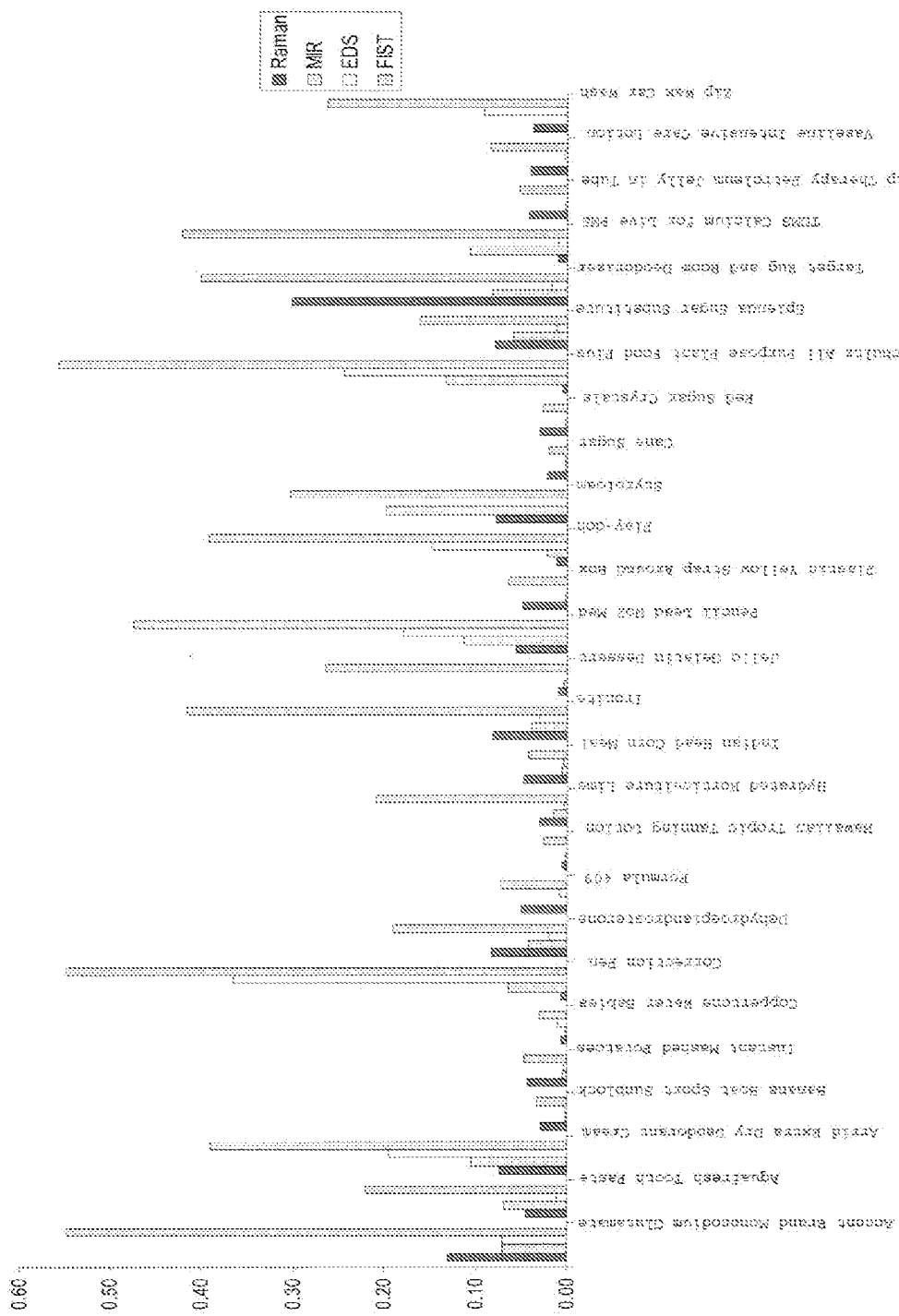

DETECTION OF PATHOGENIC MICROORGANISMS USING FUSED SENSOR DATA

RELATED APPLICATIONS

Figure 1:
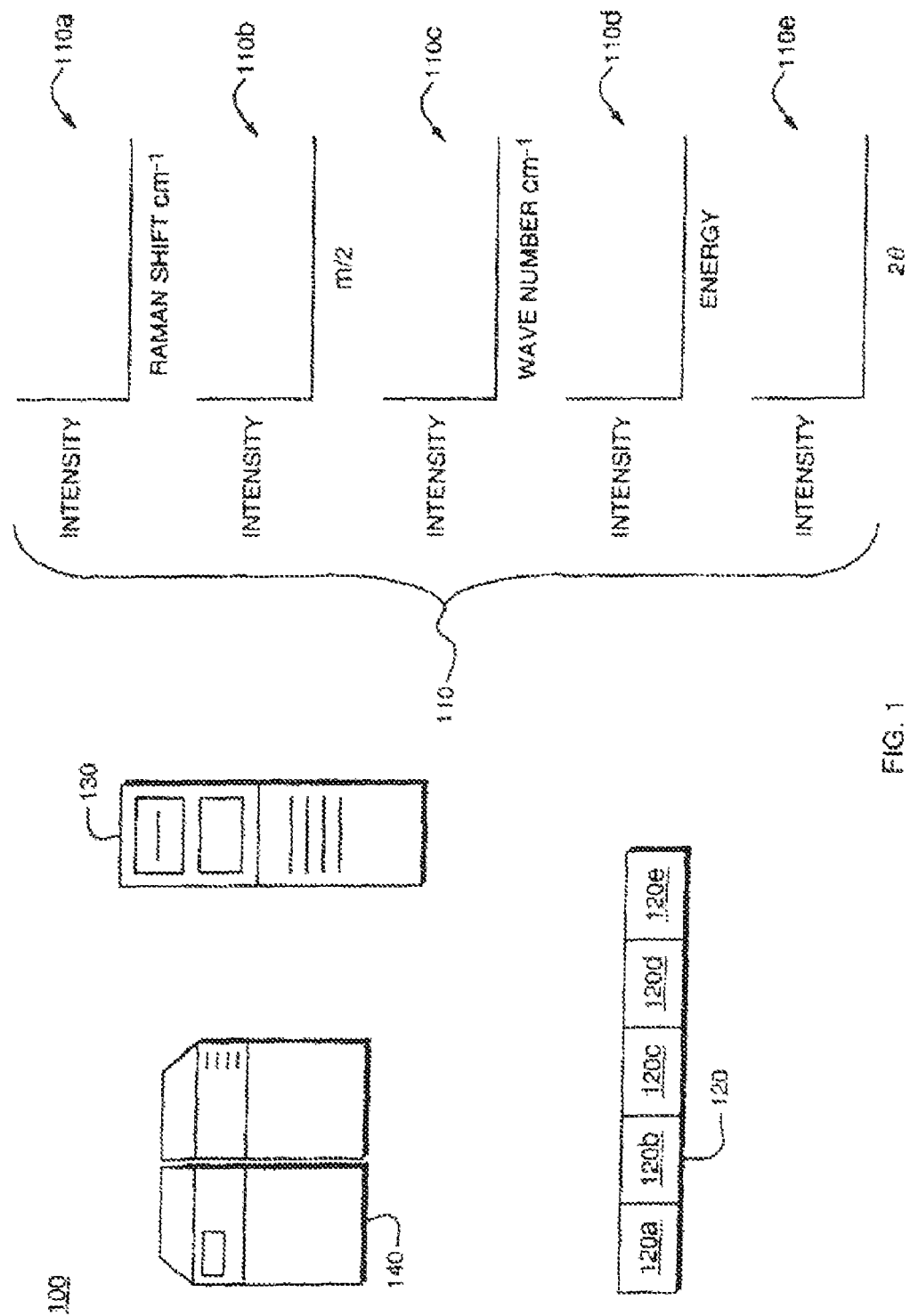

This application claims the benefit of U.S. Provisional Application No. 61/015,532, filed Dec. 20, 2007, entitled "Detection of Pathogenic Microorganisms Using Fused Sensor Data", and is a continuation-in-part of pending U.S. application Ser. No. 11/450,138, filed on Jun. 9, 2006, entitled "Forensic Integrated Search Technology", which itself claims filing date priority to U.S. Provisional Application No. 60/688,812, filed on Jun. 9, 2005, entitled "Forensic Integrated Search Technology (FIST)" and U.S. Provisional Application No. 60/711,593, filed Aug. 26, 2005, entitled "Forensic Integrated Search Technology (FIST)", and additionally, the instant application is a continuation-in-part of U.S. patent application Ser. No. 12/191,496, now U.S. Pat. No. 7,623,232, entitled "Raman Spectral Analysis of Pathogens", filed Aug. 14, 2008, which itself is a continuation of U.S. patent application Ser. No. 11/206,007, filed on Aug. 17, 2005, now U.S. Pat. No. 7,428,045, entitled "Raman Spectral Analysis of Pathogens." which itself is a continuation-in-part of U.S. patent application Ser. No. 10/922,006, filed Aug. 18, 2004, now U.S. Pat. No. 6,950,184, "Water Quality Monitoring By Raman Spectral Analysis," which itself is a continuation-in-part of U.S. patent application Ser. No. 10/823,902, filed on Apr. 14, 2004, now U.S. Pat. No. 6,917,423, entitled "Method for Detection of Pathogenic Microorganisms," which itself is a continuation of U.S. patent application Ser. No. 10/339,807, filed on Jan. 10, 2003, now U.S. Pat. No. 6,765,668, entitled "Method for Detection of Pathogenic Microorganisms," which claims priority to U.S. Provisional Patent Application No. 60/347,806, filed on Jan. 10, 2002, entitled "Rapid Spectroscopic Determination of Biological and Chemical Threats." Each of the above referenced patents and patent applications are herein incorporated by reference in their entireties.

FIELD OF DISCLOSURE

This application relates generally to systems and methods for searching spectral databases to detect and identify pathogenic microorganisms using fused sensor data.

BACKGROUND

Current genetic and molecular-based methodologies for identification of biological threat organisms from complex environmental backgrounds lack the capability for rapid reagentless broad based detection. This unmet, military and societal need stems from the 2001 anthrax attack, in which letters containing anthrax spores were mailed to two United States Senators and several news offices.

Conventional means of identifying pathogens using biology tools such as specific antibodies, genetic markers or propagation in culture are fundamentally slow and require significant hands-on manipulations. Most detection strategies require long sample preparations and extractions that precede analysis and many techniques require expensive reagents that are agent specific. Furthermore, as new Biological Warfare Agents (BWAs) and Chemical Warfare Agents (CWAs) are engineered, these conventional tools are likely to become less and less effective. Therefore, there is an increasing need to have methods that can rapidly and accurately detect and classify small amounts of these agents at a molecular level without coming into contact with them. Methods are also needed to help expand our understanding of the biological and chemical basis of such warfare agents and the potential impact on the human body. Furthermore, the knowledge gained through such molecular analysis helps identify new targets for therapeutic and preventative agents.

One approach that may prove beneficial is the use of multiple data types in detecting and identifying unknown materials, and specifically pathogenic microorganisms. However, the challenge of integrating multiple data types into a comprehensive database searching algorithm has yet to be adequately solved. Existing data fusion and database searching algorithms used in the spectroscopic community suffer from key disadvantages. Most notably, competing methods such as interactive searching are not scalable, and are at best semi-automated, requiring significant user interaction. For instance, the BioRAD KnowItAll® software claims an interactive searching approach that supports searching up to three different types of spectral data using the search strategy most appropriate to each data type. Results are displayed in a scatter plot format, requiring visual interpretation and restricting the scalability of the technique. Also, this method does not account for mixture component searches. Data Fusion Then Search (DFTS) is an automated approach that combines the data from all sources into a derived feature vector and then performs a search on that combined data. The data is typically transformed using a multivariate data reduction technique, such as Principle Component Analysis, to eliminate redundancy across data and to accentuate the meaningful features. This technique is also susceptible to poor results for mixtures, and it has limited capacity for user control of weighting factors.

The present disclosure describes a system and method that overcomes these disadvantages allowing users to identify unknown materials by using multiple spectroscopic data. More specifically, the present disclosure provides systems and methods to detect and identify pathogenic microorganisms using fused sensor data.

Some of the spectroscopic data that may be fused include but are not limited to Raman, infrared, and fluorescence spectroscopic data. Raman spectroscopy provides information about the vibrational state of molecules. Many molecules have atomic bonds capable of existing in a number of vibrational states. Such molecules are able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in frequency can be more easily distinguished from the Rayleigh scattered light. An apparatus for Raman Chemical Imaging (RCI) has been described by Treado in U.S. Pat. No. 6,002,476, and in U.S. patent application Ser. No. 09/619,371, now U.S. Pat. No. 6,788,860, the entirety of which is incorporated herein by reference.

Raman analysis is a vibrational spectroscopy technique that has been employed successfully as a rapid reagentless technique for the detection of microorganisms. Raman sensitivities can be on the cellular level, and the Raman specificity can be at the subspecies level. Applications of Raman spectroscopy to clinical samples have been achieved with various different enhancement techniques. The real advantage of Raman spectroscopy was achieved when digital imaging was coupled with Raman spectroscopy to allow for visualization of the molecular environment of a sample.

In fluorescence spectroscopy, photons are emitted from a material following an excitation step in which absorption of photons occurs. Experiments typically include a polychromatic excitation source such as mercury (Hg) or xenon (Xe) lamps or a monochromatic source such as a laser for sample excitation. A portion of the emitted radiation may then be directed into a dispersive monochromator to which a detector device such as a CCD is attached. By measuring the fluorescence spectrum from a material, one can deduce qualitative and quantitative information from inorganic and organic species.

Molecular UV/visible and infrared (IR) absorption spectroscopies involve the absorption of photons throughout the UV/visible and infrared spectral regions. Typical instrumentation includes a polychromatic source such as a deuterium or quartz tungsten halogen lamp, a dispersive element such as a monochromator or interferometer and a detection device such as a Si CCD or InGaAs focal plane array detector. Absorption measurements based upon UV-visible or IR radiation find a wide number of applications for both qualitative and quantitative determination of inorganic and organic species.

Spectroscopic imaging combines digital imaging and molecular spectroscopy techniques which can include Raman scattering, fluorescence, photoluminescence, ultraviolet, visible and infrared absorption spectroscopies. When applied to the chemical analysis of materials, spectroscopic imaging is commonly referred to as chemical imaging.

In many respects, Raman chemical imaging is an extension of Raman spectroscopy. Raman chemical imaging combines Raman spectroscopy and digital imaging for the molecular-specific analysis of materials. Much of the imaging performed since the development of the first Raman microprobes has involved spatial scanning of samples beneath Raman microprobes in order to construct Raman "maps" of surfaces. Historically, Raman imaging systems, have been built using this so called flying spot ("point scanning") approach, where a laser beam is focused to a spot and is scanned over the object field, or likewise a line scanning approach, where the laser spot is broadened in one direction by, for example, a cylindrical lens, and the two dimensional image formed on a CCD array has one spatial dimension and one wavelength dimension. Raman chemical imaging techniques have only recently achieved a degree of technological maturity that allows the simultaneous collection of high-resolution (spectral and spatial) data. Advancements in imaging spectrometer technology and their incorporation into microscopes that employ CCDs, holographic optics, lasers, and fiber optics have allowed Raman chemical imaging to become a practical technique for material analysis.

ChemImage's FALCON™ Raman chemical imaging microscope employs fluorescence imaging as the trigger mechanism to identify the presence of biological material and wide field illumination Raman collection optics with digital imaging detection for identification of the biologicals. An apparatus for Raman Chemical Imaging (RCI) has been described by Treado in U.S. Pat. No. 6,002,476, and U.S. Pat. No. 6,788,860, the entirety of each of which are incorporated herein by reference.

SUMMARY

The invention relates to systems and methods for searching spectral databases and identifying unknown materials, specifically pathogenic microorganisms, using fused sensor data. A library having a plurality of sublibraries is provided wherein each sublibrary contains a plurality of reference data sets generated by a corresponding one of a plurality of spectroscopic data generating instruments associated with the sublibrary. Each reference data set characterizes a corresponding known material. A plurality of test data sets is provided that is characteristic of an unknown material, wherein each test data set is generated by one or more of the plurality of spectroscopic data generating instruments used to generate the test data set. For each test data set, each sublibrary is searched where the sublibrary is associated with the spectroscopic data generating instrument used to generate the test data. A corresponding set of scores for each searched sublibrary is produced, wherein each score in the set of scores indicates a likelihood of a match between one of the plurality of reference data sets in the searched sublibrary based on the set of scores for each searched sublibrary. All relative probability values for each searched sublibrary are fused producing a set of final probability values that are used in determining whether the unknown material is represented through a known material characterized in the library. A highest final probability value is selected from the set of final probability values and compared to a minimum confidence value. If the highest final probability values are greater than or equal to the minimum confidence value, then the known material represented in the libraries having the highest final probability values is reported.

In one embodiment, the spectroscopic data generating instrument includes one or more of the following: a Raman spectrometer, an infrared spectrometer, an x-ray diffractometer, an energy dispersive x-ray analyzer, a mass spectrometer, a microscope, an image generating instrument, a chromatographic analyzer, a charge-coupled detector, and a fluorescence spectrometer. The reference data set includes one or more of the following: a Raman spectrum, an infrared spectrum, a fluorescence spectrum, an x-ray diffraction pattern, an energy-dispersive x-ray spectrum, and a mass spectrum. The test data set includes one or more of the following: a Raman spectrum characteristic of an unknown material, an infrared spectrum characteristic of an unknown material, a fluorescence spectrum characteristic of an unknown material, an x-ray diffraction pattern of an unknown material, an energy-dispersive x-ray spectrum characteristic of an unknown material, and a mass spectrum characteristic of an unknown material.

In another embodiment, each sublibrary is searched using a text query of the unknown material that compares the text query to a text description of the known material. In yet another embodiment, the plurality of sublibraries are searched using a similarity metric including one or more of the following: an Euclidean distance metric, a spectral angle mapper metric, a spectral information divergence metric, and a Mahalanobis distance metric.

In still another embodiment, an image sublibrary is provided where the library contains a plurality of reference images generated by an image generating instrument associated with the image sublibrary. A test image characterizing an unknown material is obtained, wherein the test image data is generated by the image generating instrument. The test image is compared to the plurality of reference images. Examples of reference and test images contemplated by this disclosure include but not limited to at a Raman image, a fluorescence image, an infrared image, a bright field image, and combinations thereof.

In another embodiment, the present disclosure provides further for a system and method to search spectra databases and to identify unknown materials. A library having a plurality of sublibraries is provided. Each sublibrary contains a plurality of reference data sets generated by a corresponding one of a plurality of spectroscopic data generating instruments associated with the sublibrary. Each reference data set characterizes a corresponding known material and one sublibrary comprises an image sublibrary containing a set of reference feature data. Each set of reference feature data includes one or more of the following: particle size, color value, and morphology data. A plurality of test data sets characteristic of an unknown material is obtained, wherein each test data set is generated by one of the plurality of spectroscopic data generating instruments and one test data set includes an image test data set generated by an image generating instrument. A set of test feature data is extracted from the image test data set, using a feature extraction algorithm, the test feature data including one or more of the following: particle size, color value, and morphology. For the test feature data, the image sublibrary is searched to compare each set of reference feature data with the set of test feature data to thereby produce a set of scores, wherein each score in the set of scores indicates a likelihood of a match between a corresponding set of reference feature data in the searched image sublibrary and the set of test feature data. For each test data set, each sublibrary associated with the spectroscopic data generating instrument used to generate the test data set, is searched producing a corresponding set of scores for each searched sublibrary, wherein each score in the set of scores indicates a likelihood of a match between a corresponding one of said plurality of reference data sets in the searched sublibrary and the test data set. A set of relative probability values for each searched sublibrary is calculated based on the corresponding set of scores for each searched sublibrary and a set of relative probability values for the image sublibrary based on the corresponding set of scores for the image sublibrary. All relative probability values for each searched sublibrary and searched image sublibrary are fused producing a set of final probability values to be used in determining whether the unknown material is represented through a corresponding known material characterized in the library. The known material represented in the library having the highest final probability values is reported, if the highest final probability value is greater than or equal to the minimum confidence value.

In another embodiment, if a highest final probability value is less than a minimum confidence value, the unknown material is treated as a mixture of unknown materials. A plurality of second test data sets is generated by one of the plurality of the different spectroscopic data generating instruments. The plurality of second test data sets is combined with the plurality of tests data sets to generate a plurality of combined test data sets. The combination is made such that the plurality of second test data sets and plurality of test data sets were generated by the same spectroscopic data generating instrument. For each combined test data set, each sublibrary, associated with the spectroscopic data generating instrument used to generate the combined test data set, is searched producing a corresponding second set of scores for each second searched sublibrary. Each second score in the second set of scores indicates a second likelihood of a match between a corresponding one of the plurality of reference data sets in the second searched sublibrary and each combined test data set. A second set of relative probability values is calculated for each searched sublibrary based on the corresponding second set of scores for each searched sublibrary. All second relative probabitly values to be used in determining whether the unknown material is represented through a corresponding set of known materials in the library.

Examples of pathogens (e.g., human pathogens or those of animals or plants) that can be assessed using the methods described herein include bacteria (including eubacteria and archaebacteria), eukaryotic microorganisms (e.g., protozoa, fungi, yeasts, and molds) viruses, and biological toxins (e.g., bacterial or fungal toxins or plant lectins). Specific examples of such pathogens include protozoa of the genus *Cryptosporidium*, protozoa of the genus *Giardia*, bacteria of genera such as *Escherichia, Escherichia coli, Escherichia coli* 157, *Yersinia, Francisella, Brucella, Clostridium, Burkholderia, Chlamydia, Coxiella, Rickettsia, Vibrio, Enterococcus, Staphylococcus, Staphylococcus*, methicillin-resistant staphylococcus (MRSA), *Enterobacter, Corynebacterium, Pseudomonas, Acinetobacter, Klebsiella*, and *Serratia*. Assessable organisms include at least *Escherichia coli, Yersinia pestis. Francisella tularensis, Clostridium perfringens, Burkholderia mallei, Burkholderia pseudomallei*, cryptosporidia microorganisms, Tularemia (*Francisella tularensis*), Brucellosis (*Brucella* species), Chlamydia psittaci (psittacosis), *Coxiella burneti* (Q fever), *Rickettsia prowazeki* (Typhus fever), *Vibrio vulnificus, Vibrio enteralyticus, Vibrio fischii, Vibrio cholera, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens, Candida albicans, Microsporum audouini, Microsporum canis, Microsporum gypseum, Trichophyton mentagrophytes* var. *mentagrophytes, Trichophyton mentagrophytes* var. *interdigitale, Trichophyton rubrum, Trichophyton tonsurans, Trichophyton verrucosum*, and *Epidermophytum floccosum*, Streptococcus (including Strep A, B, C, G) filoviruses such as Ebola and Marburg viruses, naviruses such as Lassa fever and Machupo viruses, alphaviruses such as Venezuelan equine encephalitis, eastern equine encephalitis, and western equine encephalitis, rotaviruses, calciviruses such as Norwalk virus, and hepatitis (A, B, and C) viruses.

In one embodiment, the methods described herein can be used to assess a biological warfare agent. Examples of agents that can be assessed using these methods include at least *Bacillus anthracis, Bartonella quintana, Brucella melitensis, Burkholderia mallei, Burkholderia pseudomallei, Chlamydia psittaci, Clostridium botulinum, Clostridium perfringens, Coxiella burnetti*, enterohemorrhagic *Escherichia coli, Francisella tularensis, Rickettsia mooseri, Rickettsia prowasecki, Rickettsia rickettsii, Rickettsia tsutsugamushii, Salmonella typhi, Salmonella, Shigella, Shigella dysenteriae, Vibrio cholerae, Yersinia pestis, Coccidioides immitis, Histoplasma capsulatum*, chikungunya virus, Congo-Crimean haemorrhagic fever virus, dengue fever virus, Eastern equine encephalitis virus, ebola virus, equine morbillivirus, hantaan virus, Japanese encephalitis virus, junin virus, lassa fever virus, Epstein Barr virus (infectious mononucleosis), lymphocytic choriomeningitis virus, machupo virus, marburg virus, monkey pox virus, Murray valley encephalitis virus, nipah virus, Omsk hemorrhagic fever virus, oropouche virus, Rift valley fever virus, Russian Spring-Summer encephalitis virus, smallpox virus, South American hemorrhagic fever viruses, St. Louis encephalitis virus, tick-borne encephalitis virus. Variola virus, Venezuelan equine encephalitis virus, Western equine encephalitis virus, white pox virus, yellow fever virus, botulinum toxins, *Clostridium perfringens* toxins, microcystins (Cyanginosins), Shiga toxin, verotoxin, Staphylococcal enterotoxin B, anatoxin A, conotoxins, palytoxin, saxitoxin, tetrodotoxin, stachybotrys toxins, aflatoxins, trichothecenes, satratoxin H, T-2 toxin, and ricin. Other examples include *Abrus precatorius* lectin, African swine fever virus, avian influenza virus, banana bunchy top virus, bluetongue virus, camelpox virus, cholera toxin, *Clostridium perfringens, Clostridium tetani, Cryptosporidium parvum, Deuterophoma tracheiphila, Entamoeba histolytica*, ergot alkaloids, *Escherichia coli* 0157, foot and mouth disease virus, *Giardia, Giardia lamblia*, goat pox virus, hendra virus, hepatitis A virus, hog cholera virus, human immunodeficiency virus, infectious conjunctivitis virus, influenza virus (including influenza A, influenza B, and influenza C viruses), Kyasanur Forest virus, *Legionella pneumophila*, louping ill virus, lyssaviruses, *Adenia digitata* lectin (modeccin), *Monilia rorei, Naegleria fowleri*, nipah virus, Murray Valley encephalitis virus, *Mycoplasma mycoides*, newcastle disease virus, oropouche virus, peste des petits ruminants virus, porcine enterovirus 9, powassan virus, pseudorabies virus, rinderpest virus, rocio virus, group B rotaviruses, *Salmonella paratyphi*, sheeppox virus, St. Louis encephalitis virus, substance P, *Serratia marcescens*, Teschen-Talfan virus, tetanus toxin, vesicular stomatitis virus, *Visctim album* lectin 1 (Viscumin), *Adena volkensii* lectin (volkensin), West Nile virus, *Xanthomonas campestris* oryzae, *Xylella fastidiosa*, and *Yersinia pseudotuberculosis*.

Examples of plant pathogens that can be assessed using these methods include at least *Burkholderia solanacearum*, citrus greening disease bacteria, *Erwinia amylovora, Xanthomonas albilineans, Xanthomonas axonopodis* pv. *citri, Bipolaris* (Helminthosporium) *maydis, Claviceps purpurea, Colletotrichum coffeanum virulans, Cochliobolus miyabeanus, Dothistroma pini, Fusarium oxysporum, Microcystis ulei, Neovossia indica, Peronospora hyoscyami, Puccinia erianthi, Puccinia graminis, Puccinia graminis* f. sp. *tritici, Puccinia striifonnis, Pyricularia grisea, Sclerotinia sclerotiorum, Sclerotium rolfsii, Tilletia indica, Ustilago maydis, Phytophthora infestans*, and Fiji disease virus.

In addition to assessing occurrence of a pathogen in a sample, the methods described herein can be used to distinguish among various pathogens, to distinguish between viable and non-viable forms of the same pathogen, and to distinguish between infectious and non-infectious forms of the same pathogen. Furthermore, the assessment methods described herein can be coupled with pathogen-ablating methods to ablate or eliminate pathogens from a sample.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principle of the disclosure.

In the drawings:

FIG. 1 illustrates a system of the present disclosure.

FIG. 2 illustrates a method of the present disclosure.

FIG. 3 illustrates a method of the present disclosure.

FIG. 4 illustrates a method of the present disclosure.

FIGS. 5A-5D illustrates the ability to discriminate and identify major bacteria of concern on the CDC category A and B list of pathogens as well as the toxin ricin. Bright field images of sample pathogens are represented in FIG. 5A. Raman spectra of the samples are represented in FIG. 5B. FIG. 5C is an exemplary Mahalanobis differential classification scheme as applied to the data. FIG. 5D is an exemplary dendrogram showing the linkage of the materials.

FIG. 6 is an exemplary breakdown of a Raman signature library.

Figure 7:
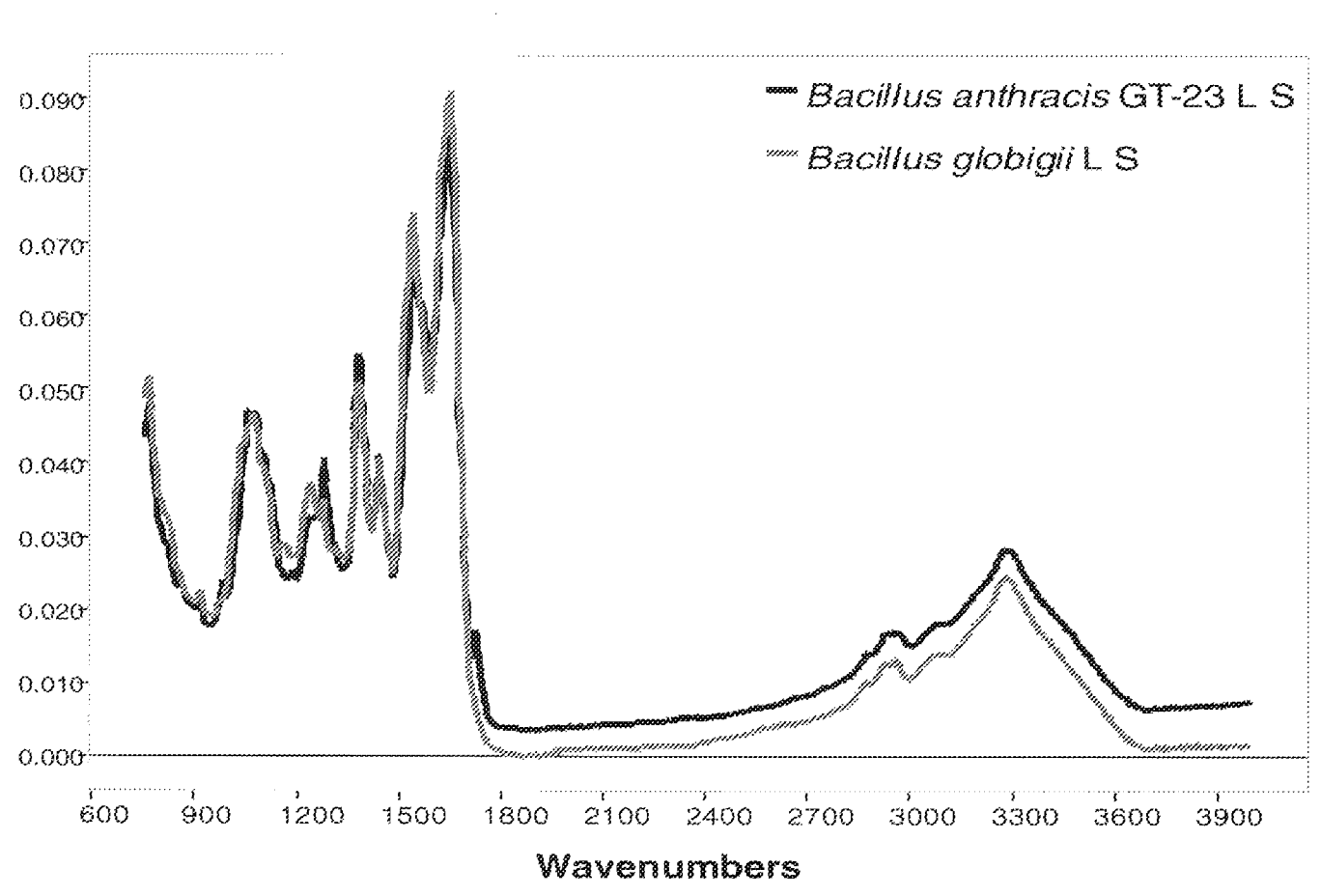

FIG. 7 illustrates the ability to distinguish between two *Bacillus* species, *Bacillus anthracis* and *Bacillus globigii*, using Infrared Absorption Spectrscopy (IR).

FIG. 8 illustrates how fluorescence imaging can be used to discriminate *Bacillus globigii* and *Bacillus stereothermophilus* using both morphology and spectrometry.

FIG. 9 illustrates discrimination performance of using Raman as a detection phenomenology as well as a confusion matrix image for the comprehensive signature library.

FIG. 10 illustrates the results of performing a spectral search for mid-infrared spectra, energy dispersive spectra (EDS), and Raman spectra of 27 commercial products.

DETAILED DESCRIPTION OF THE DISCLOSURE

Reference will now be made in detail to the preferred embodiments of the present disclosure, examples of which are illustrated in the accompanying drawings. Wherever possible, the same reference numbers will be used throughout the drawings to refer to the same or like parts.

FIG. 1 illustrates an exemplary system 100 which may be used to carry out the methods of the present disclosure. System 1 includes a plurality of test data sets 110, a library 120, at least one processor 130 and a plurality of spectroscopic data generating instruments 140. The plurality of test data sets 110 includes data that are characteristic of an unknown material. The composition of the unknown material includes a single chemical composition or a mixture of chemical compositions.

The plurality of test data sets 110 includes data that characterizes an unknown material. The plurality of test data sets 110 are obtained from a variety of instruments 140 that produce data representative of the chemical and physical properties of the unknown material. The plurality of test data sets includes spectroscopic data, text descriptions, chemical and physical property data, and chromatographic data. In one embodiment, the plurality of test data sets includes a spectrum or a pattern that characterizes the chemical composition, molecular composition, physical properties and/or elemental composition of an unknown material. In another embodiment, the plurality of test data sets includes one or more of a Raman spectrum, a infrared spectrum, an x-ray diffraction pattern, an energy dispersive x-ray spectrum, a fluorescence spectrum, and a mass spectrum, all characteristic of the unknown material. In yet another embodiment, the plurality of test data sets also includes an image data set of the unknown material. The image is selected from the group consisting of a Raman image, a florescence image, an infrared image, a bright field image, and combinations thereof. In still another embodiment, the test data set includes a physical property test data set selected from the group consisting of boiling point, melting point, density, freezing point, solubility, refractive index, specific gravity or molecular weight of the unknown material. In another embodiment, the test data set includes a textual description of the unknown material.

The plurality of spectroscopic data generating instruments 140 include any analytical instrument which generates a spectrum, an image, a chromatogram, a physical measurement and a pattern characteristic of the physical properties, the chemical composition, or structural composition of a material. In one embodiment, the plurality of spectroscopic data generating instruments 140 includes a Raman spectrometer, an infrared spectrometer, an x-ray diffractometer, an energy dispersive x-ray analyzer and a mass spectrometer. In another embodiment, the plurality of spectroscopic data generating instruments 140 further includes a microscope or image generating instrument. In yet another embodiment, the plurality of spectroscopic generating instruments 140 further includes a chromatographic analyzer.

Library 120 includes a plurality of sublibraries 120a, 120b, 120c, 120d and 120e. Each sublibrary is associated with a different spectroscopic data generating instrument 140. In one embodiment, the sublibraries include a Raman sublibrary, an infrared sublibrary, an x-ray diffraction sublibrary, an energy dispersive sublibrary and a mass spectrum sublibrary. For this embodiment, the associated spectroscopic data generating instruments 140 include a Raman spectrometer, an infrared spectrometer, an x-ray diffractometer, an energy dispersive x-ray analyzer and a mass spectrometer. In another embodiment, the sublibraries further include an image sublibrary associated with a microscope. In yet another embodiment, the sublibraries further include a textual description sublibrary. In still yet another embodiment, the sublibraries further include a physical property sublibrary.

Each sublibrary contains a plurality of reference data sets. The plurality of reference data sets includes data representative of the chemical and physical properties of a plurality of known materials. The plurality of reference data sets includes spectroscopic data, text descriptions, chemical and physical property data, and chromatographic data. In one embodiment, a reference data set includes a spectrum and a pattern that characterizes the chemical composition, the molecular composition and/or element composition of a known material. In another embodiment, the reference data set includes a Raman spectrum, an infrared spectrum, an x-ray diffraction pattern, an energy dispersive x-ray spectrum, and a mass spectrum of known materials. In yet another embodiment, the reference data set further includes a physical property test data set of known materials selected from the group consisting of boiling point, melting point, density, freezing point, solubility, refractive index, specific gravity or molecular weight. In still another embodiment, the reference data set further includes an image displaying the shape, size and morphology of known materials. In another embodiment, the reference data set includes feature data having information such as particle size, color and morphology of the known material.

System 100 further includes at least one processor 130 in communication with the library 120 and sublibraries. The processor 130 executes a set of instructions to identify the composition of an unknown material.

In one embodiment, system 100 includes a library 120 having the following sublibraries: a Raman sublibrary associated with a Raman spectrometer; an infrared sublibrary associated with an infrared spectrometer; an x-ray diffraction sublibrary associated with an x-ray diffractometer; an energy dispersive x-ray sublibrary associated with an energy dispersive x-ray spectrometer; and a mass spectrum sublibrary associated with a mass spectrometer. The Raman sublibrary contains a plurality of Raman spectra characteristic of a plurality of known materials. The infrared sublibrary contains a plurality of infrared spectra characteristic of a plurality of known materials. The x-ray diffraction sublibrary contains a plurality of x-ray diffraction patterns characteristic of a plurality of known materials. The energy dispersive sublibrary contains a plurality of energy dispersive spectra characteristic of a plurality of known materials. The mass spectrum sublibrary contains a plurality of mass spectra characteristic of a plurality of known materials. The test data sets include two or more of the following: a Raman spectrum of the unknown material, an infrared spectrum of the unknown material, an x-ray diffraction pattern of the unknown material, an energy dispersive spectrum of the unknown material, and a mass spectrum of the unknown material. In another embodiment, the test data sets include at least one of the following: a Raman spectrum of the unknown material, an infrared spectrum of the unknown material, an x-ray diffraction pattern of the unknown material, an energy dispersive spectrum of the unknown material, and a mass spectrum of the unknown material.

Figure 2:
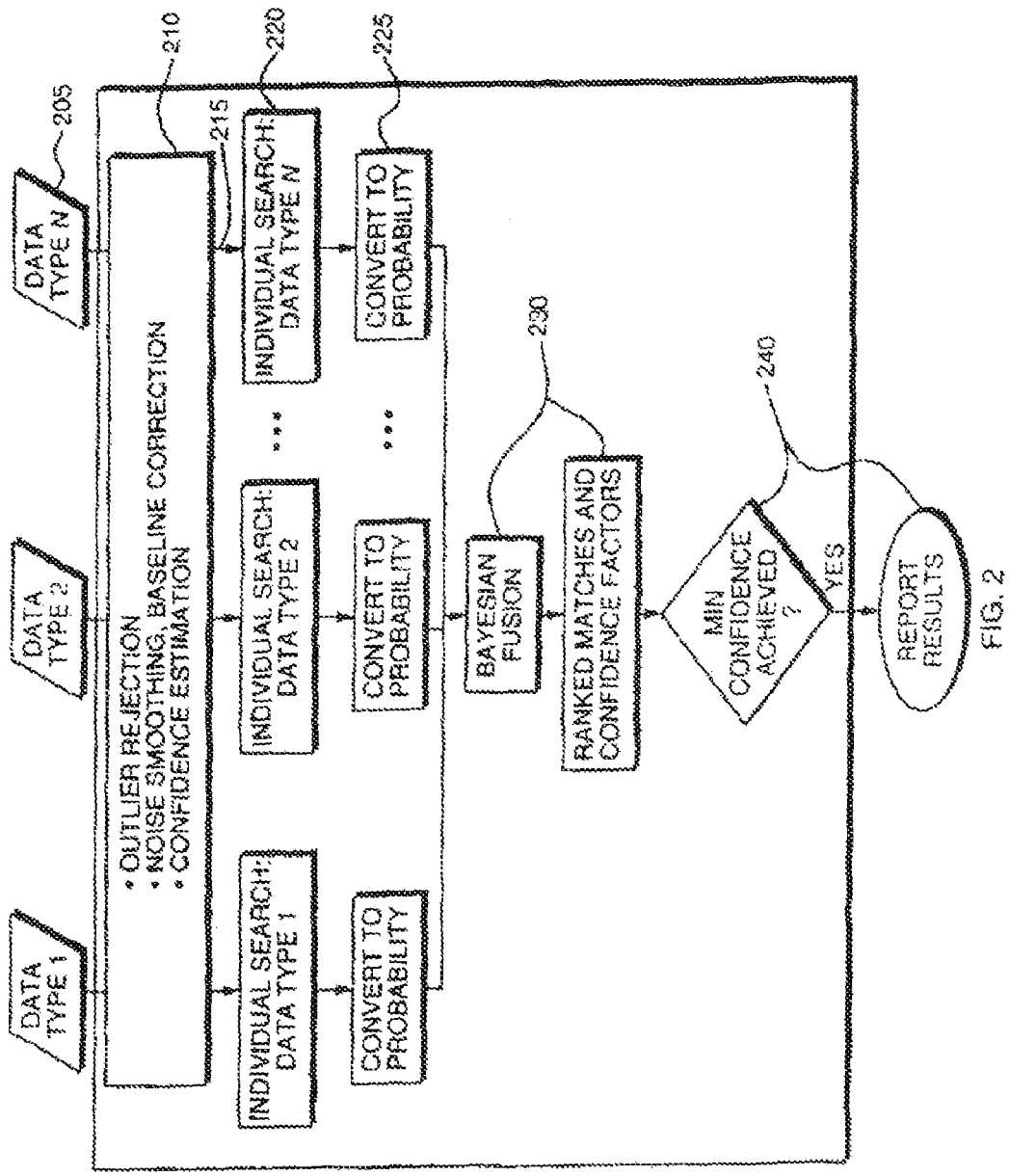

With reference to FIG. 2, a method of the present disclosure is illustrated to determine the identification of an unknown material. In step 205, a plurality of test data sets characteristic of an unknown material are obtained by at least one of the different spectroscopic data generating instruments. In one embodiment, the plurality of test data sets 110 are obtained from one or more of the different spectroscopic data generating instruments 140. When a single spectroscopic data generating instrument is used to generate the test data sets, at least two or more test data sets are required. In yet another embodiment, the plurality of test data sets 110 are obtained from at least two different spectroscopic data generating instruments.

In step 210, the test data sets are corrected to remove signals and information that are not due to the chemical composition of the unknown material. Algorithms known to those skilled in the art are applied to the data sets to remove electronic noise and to correct the baseline of the test data set. The data sets are also be corrected to reject outlier data sets. In one embodiment, the system detects test data sets, having signals and information that are not due to the chemical composition of the unknown material. These signals and information are then removed from the test data sets. In another embodiment, the user is issued a warning when the system detects test data set having signals and information that are not due to the chemical composition of the unknown material.

With further reference to FIG. 2, each sublibrary is searched, in step 220. The searched sublibraries are those that are associated with the spectroscopic data generating instrument used to generate the test data sets. For example, when the plurality of test data sets includes a Raman spectrum of the unknown material and an infrared spectrum of the unknown material, the system searches the Raman sublibrary and the infrared sublibrary. The sublibrary search is performed using a similarity metric that compares the test data set to each of the reference data sets in each of the searched sublibraries. In one embodiment, any similarity metric that produces a likelihood score is used to perform the search. In another embodiment, the similarity metric includes one or more of an Euclidean distance metric, a spectral angle mapper metric, a spectral information divergence metric, and a Mahalanobis distance metric. The search results produce a corresponding set of scores for each searched sublibrary. The set of scores contains a plurality of scores, one score for each reference data set in the searched sublibrary. Each score in the set of scores indicates a likelihood of a match between the test data set and each of reference data set in the searched sublibrary.

In step 225, the set of scores, produced in step 220, are converted to a set of relative probability values. The set of relative probability values contains a plurality of relative probability values, one relative probability value for each reference data set.

Referring still to FIG. 2, all relative probability values for each searched sublibrary are fused, in step 230, using the Bayes probability rule. The fusion produces a set of final probability values. The set of final probability values contains a plurality of final probability values, one for each known material in the library. The set of final probability values is used to determine whether the unknown material is represented by a known material in the library.

In step 240, the identity of the unknown material is reported. To determine the identity of the unknown, the highest final probability value from the set of final probability values is selected. This highest final probability value is then compared to a minimum confidence value. If the highest final probability value is greater than or equal to the minimum confidence value, the known material having the highest final probability value is reported. In one embodiment, the minimum confidence value ranges from 0.70 to 0.95. In another embodiment, the minimum confidence value ranges from 0.8 to 0.95. In yet another embodiment, the minimum confidence value ranges from 0.90 to 0.95.

As described above, the library 120 contains several different types of sublibraries, each of which is associated with an analytical technique, i.e., the spectroscopic data generating instrument 140. Therefore, each analytical technique provides an independent contribution to identifying the unknown material. Additionally, each analytical technique has a different level of specificity for matching a test data set for an unknown material with a reference data set for a known material. For example, a Raman spectrum generally has higher discriminatory power than a fluorescence spectrum and is thus considered more specific for the identification of an unknown material. The greater discriminatory power of Raman spectroscopy manifests itself as a higher likelihood for matching any given spectrum using Raman spectroscopy than using fluorescence spectroscopy. The method illustrated in FIG. 2 accounts for this variability in discriminatory power in the set of scores for each spectroscopic data generating instrument. The set of scores act as implicit weighting factors that bias the scores according to the discriminatory power of the instrument. While the set of scores act as implicit weighting factors, the method of the present disclosure also provides for using explicit weighting factors. In one embodiment, the explicit weighting factor for each spectroscopic data generating instrument is the same. In another embodiment the weighting factors include $\{W\}=\{W_{Raman}, W_{x-ray}, W_{MassSpec}, W_{IR}, \text{ and } W_{ED}\}$.

In yet another embodiment, each spectroscopic data generating instrument has a different associated weighting factor. Estimates of these associated weighting factors are determined through automated simulations. In particular, with at least two data records for each spectroscopic data generating instrument (i.e. two Raman spectra per material), the library is split into training and validation sets. The training set is then used as the reference data set. The validation set is used as test data set and searched against the training set. Without the weighting factors ($\{W\}=\{1, 1, \ldots, 1\}$), a certain percentage of the validation set will be correctly identified, and some percentage will be incorrectly identified. By explicitly or randomly varying the weighting factors and recording each set of correct and incorrect identification rates, the optimal operating set of weighting factors, for each spectroscopic data generating instrument, is estimated by choosing those weighting factors that result in the best identification rates.

The method of the present disclosure also provides for using a text query to limit the number of reference data sets of known compounds in the sublibrary searched in step 220 of FIG. 2. The method illustrated in FIG. 2, would further include step 215, where each sublibrary is searched, using a text query. Each known material in the plurality of sublibraries includes a text description of a physical property or a distinguishing feature of the material. A text query, describing the unknown material is submitted. The plurality of sublibraries is searched by comparing the text query to a text description of each of the known materials. A match of the text query to the text description or no match of the text query to the text description is produced. The plurality of sublibraries is modified by removing the reference data sets that produced a no match answer. Therefore, the modified sublibraries have fewer reference data sets than the original sublibraries. For example, a text query for white powders eliminates the reference data sets from the sublibraries for any known compounds having a textual description of black powders. The modified sublibraries are then searched as described for steps 220-240 as illustrated in FIG. 2.

The method of the present disclosure also provides for using images to identify the unknown material. In one embodiment, an image test data set characterizing an unknown material is obtained from an image generating instrument. The test image, of the unknown, is compared to the plurality of reference images for the known materials in an image sublibrary to assist in the identification of the unknown material. In another embodiment, a set of test feature data is extracted from the image test data set using a feature extraction algorithm to generate test feature data. The selection of an extraction algorithm is well known to one of skill in the art of digital imaging. The test feature data includes information concerning particle size, color or morphology of the unknown material. The test feature data is searched against the reference feature data in the image sublibrary, producing a set of scores. The reference feature data includes information such as particle size, color and morphology of the material. The set of scores, from the image sublibrary, are used to calculate a set of probability values. The relative probability values, for the image sublibrary, are fused with the relative probability values for the other plurality of sublibraries as illustrated in FIG. 2, step 230, producing a set of final probability values. The known material represented in the library, having the highest final probability value is reported if the highest final probability value is greater than or equal to the minimum confidence value as in step 240 of FIG. 2.

The method of the present disclosure further provides for enabling a user to view one or more reference data sets of the known material identified as representing the unknown material despite the absence of one or more test data sets. For example, the user inputs an infrared test data set and a Raman test data set to the system. The x-ray dispersive spectroscopy ("EDS") sublibrary contains an EDS reference data set for the plurality of known compounds even though the user did not input an EDS test data set. Using the steps illustrated in FIG. 2, the system identifies a known material, characterized in the infrared and Raman sublibraries, as having the highest probability of matching the unknown material. The system then enables the user to view an EDS reference data set, from the EDS sublibrary, for the known material having the highest probability of matching the unknown material. In another embodiment, the system enables the user to view one or more EDS reference data sets for one or more known materials having a high probability of matching the unknown material.

The method of the present disclosure also provides for identifying unknowns when one or more of the sublibraries are missing one or more reference data sets. When a sublibrary has fewer reference data sets than the number of known materials characterized within the main library, the system treats this sublibrary as an incomplete sublibrary. To obtain a score for the missing reference data set, the system calculates a mean score based on the set of scores, from step 225, for the incomplete library. The mean score is then used, in the set of scores, as the score for missing reference data set.

The method of the present disclosure also provides for identifying miscalibrated test data sets. When one or more of the test data sets fail to match any reference data set in the searched sublibrary, the system treats the test data set as miscalibrated. The assumed miscalibrated test data sets are processed via a grid optimization process where a range of zero and first order corrections are applied to the data to generate one or more corrected test data sets. The system then reanalyzes the corrected test data set using the steps illustrated in FIG. 2. This same process is applied during the development of the sublibraries to ensure that all the library spectra are properly calibrated. The sublibrary examination process identifies referenced data sets that do not have any close matches, by applying the steps illustrated in FIG. 2, to determine if changes in the calibration results in close matches.

Figure 3:
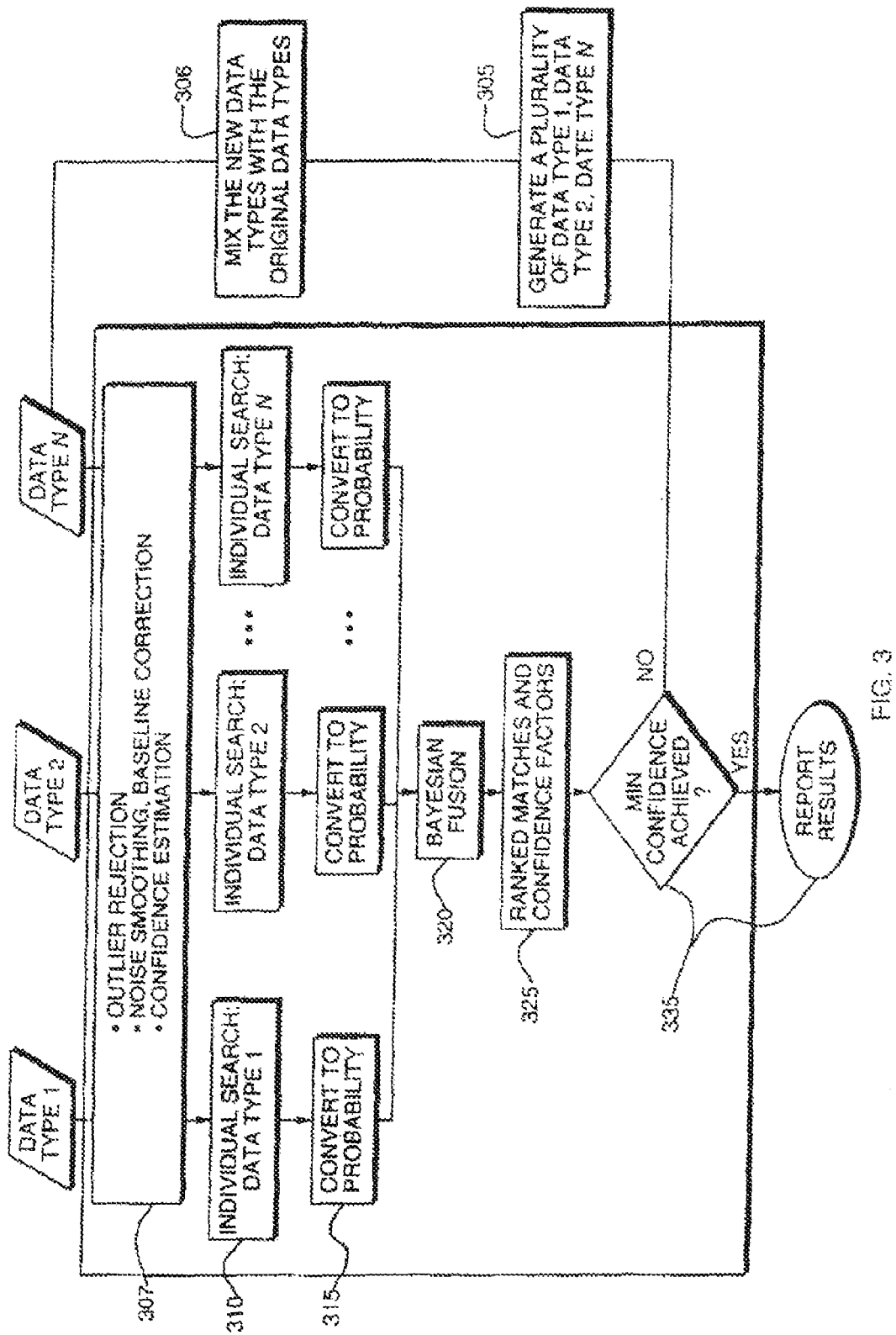

The method of the present disclosure also provides for the identification of the components of an unknown mixture. With reference to FIG. 2, if the highest final probability value is less than the minimum confidence value, in step 240, the system of the present disclosure treats the unknown as a mixture. Referring to FIG. 3, a plurality of new test data sets, characteristic of the unknown material, are obtained in step 305. Each new test data set is generated by one of the plurality of the different spectroscopic data generating instruments. For each different spectroscopic data generating instruments at least two new test data sets are obtained. In one embodiment, six to twelve new test data sets are obtained from a spectroscopic data generating instrument. The new test data sets are obtained from several different locations of the unknown. The new test data sets are combined with the test data sets, of step 205 in FIG. 2, to generate combined test data sets, of step 306 of FIG. 3. When the test data sets are combined with the new test data sets, the sets must be of the same type in that they are generated by the same spectroscopic data generating instrument. For example, new test data sets generated by a Raman spectrometer are combined with the initial test data sets also generated by a Raman spectrometer.

In step 307, the test data sets are corrected to remove signals and information that are not due to the chemical composition of the unknown material. In step 310, each sublibrary is searched for a match for each combined test data set. The searched sublibraries are associated with the spectroscopic data generating instrument used to generate the combined test data sets. The sublibrary search is performed using a spectral unmixing metric that compares the plurality of combined test data sets to each of the reference data sets in each of the searched sublibraries. A spectral unmixing metric is disclosed in U.S. patent application Ser. No. 10/812,233 entitled "Method for Identifying Components of a Mixture via Spectral Analysis," filed Mar. 29, 2004, now U.S. Pat. No. 7,072,770, which is incorporated herein by reference in its entirety; however this application forms no part of the present invention. The sublibrary searching produces a corresponding second set of scores for each searched sublibrary. Each second score and the second set of scores is the score and set of scores produced in the second pass of the searching method. Each second score in the second set of scores indicates a second likelihood of a match between the combined test data sets and each of reference data sets in the searched sublibraries. The second set of scores contains a plurality of second scores, one second score for each reference data set in the searched sublibrary.

According to a spectral unmixing metric, the combined test data sets define an n-dimensional data space, where n is the number of points in the test data sets. Principal component analysis (PCA) techniques are applied to the n-dimensional data space to reduce the dimensionality of the data space. The dimensionality reduction step results in the selection of m eigenvectors as coordinate axes in the new data space. For each search sublibrary, the reference data sets are compared to the reduced dimensionality data space generated from the combined test data sets using target factor testing techniques. Each sublibrary reference data set is projected as a vector in the reduced m-dimensional data space. An angle between the sublibrary vector and the data space results from target factor testing. This is performed by calculating the angle between the sublibrary reference data set and the projected sublibrary data. These angles are used as the second scores which are converted to second probability values for each of the reference data sets and fed into the fusion algorithm in the second pass of the search method. This paragraph forms no part of the present invention.

Referring still to FIG. 3, second relative probability values are determined and the values are then fused. A second set of relative probability values are calculated for each searched sublibrary based on the corresponding second set of scores for each searched sublibrary, step 315. The second set of relative probability values is the set of probability values calculated in the second pass of the search method. The second relative probability values for each searched sublibrary are fused using the Bayes probability rule to produce a second set of final probability values, step 320. The set of final probability values are used in determining whether the unknown materials are represented by a set of known materials in the library.

From the set of second final probabilities values, a set of high second final probability values is selected. The set of high second final probability values is then compared to the minimum confidence value, step 325. If each high second final probability value is greater than or equal to the minimum confidence value, step 335, the set of known materials represented in the library having the high second final probability values is the reported. In one embodiment, the minimum confidence value ranges from 0.70 to 0.95. In another embodiment, the minimum confidence value may range from 0.8 to 0.95. In yet another embodiment, the minimum confidence value may range from 0.9 to 0.95.

Figure 4:
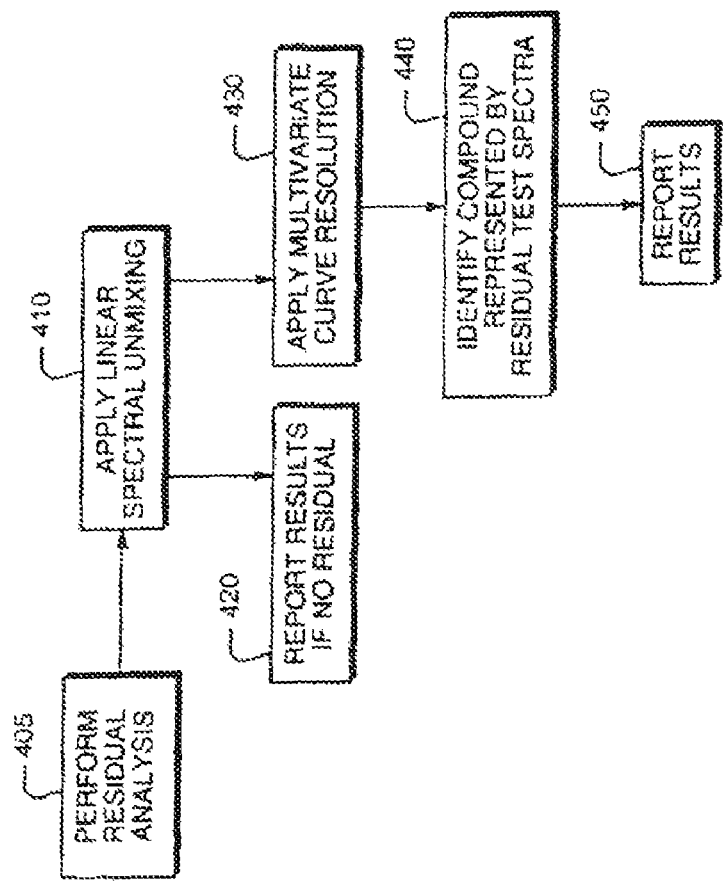

Referring to FIG. 4, a user may also perform a residual analysis. For each spectroscopic data generating instrument, residual data is defined by the following equation:

$$\text{COMBINED TEST DATA SET} = \text{CONCENTRATION} \times \text{REFERENCE DATA SET} + \text{RESIDUAL}$$

To calculate a residual data set, a linear spectral unmixing algorithm is applied to the plurality of combined test data sets, to thereby produce a plurality of residual test data, step 410. Each searched sublibrary has an associated residual test data. When a plurality of residual data are not identified in step 410, a report is issued, step 420. In this step, the components of the unknown material are reported as those components determined in step 335 of FIG. 3. Residual data is determined when there is a significant percentage of variance explained by the residual as compared to the percentage explained by the reference data set defined in the above equation. When residual test data is determined in step 410, a multivariate curve resolution algorithm is applied to the plurality of residual test data generating a plurality of residual data spectra, in step 430. Each searched sublibrary has a plurality of associated residual test spectra. In step 440, the identification of the compound corresponding to the plurality of residual test spectra is determined and reported in step 450. In one embodiment, the plurality of residual test spectra are compared to the reference data set in the sublibrary, associated with the residual test spectra, to determine the compound associated with the residual test spectra. If residual test spectra do not match any reference data sets in the plurality of sublibraries, a report is issued stating an unidentified residual compound is present in the unknown material.

The systems and methods of the present disclosure may be used to search spectral databases to identify unknown materials, specifically pathogenic microorganisms, using fused sensor data. Exemplary pathogens (e.g., human pathogens or those of animals or plants) include bacteria (including eubacteria and archaebacteria), eukaryotic microorganisms (e.g., protozoa, fungi, yeasts, and molds) viruses, and biological toxins (e.g., bacterial or fungal toxins or plant lectins). Specific examples of such pathogens include protozoa of the genus *Cryptosporidium*, protozoa of the genus *Giardia*, bacteria of genera such as *Escherichia, Escherichia coli, Escherichia coli* 157, *Yersinia, Francisella, Brucella, Clostridium, Burkholderia, Chlamydia, Coxiella, Rickettsia, Vibrio, Enterococcus, Staphylococcus, Staphylococcus*, methicillin-resistant staphylococcus (MRSA), *Enterobacter, Corynebacterium, Pseudomonas, Acinetobacter, Klebsiella*, and *Serratia*. Assessable organisms include at least *Escherichia coli, Yersinia pestis. Francisella tularensis, Clostridium perfringens, Burkholderia mallei, Burkholderia pseudomallei*, cryptosporidia microorganisms, *Tularemia (Francisella tularensis)*, Brucellosis (*Brucella* species), *Chlamydia psittaci* (psittacosis), *Coxiella burneti* (Q fever), *Rickettsia prowazeki* (Typhus fever), *Vibrio vulnificus, Vibrio enteralyticus, Vibrio fischii, Vibrio cholera, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens, Candida albicans, Microsporum audouini, Microsporum canis, Microsporum gypseum, Trichophyton mentagrophytes* var. *mentagrophytes, Trichophyton mentagrophytes* var. *interdigitale, Trichophyton rubrum, Trichophyton tonsurans, Trichophyton verrucosum*, and *Epidermophytum floccosum*, Streptococcus (including Strep A, B, C, G) filoviruses such as Ebola and Marburg viruses, naviruses such as Lassa fever and Machupo viruses, alphaviruses such as Venezuelan equine encephalitis, eastern equine encephalitis, and western equine encephalitis, rotaviruses, calciviruses such as Norwalk virus, and hepatitis (A, B, and C) viruses.

In one embodiment, the unknown materials include a biological warfare agent. Examples of such agents include at least *Bacillus anthracis, Bartonella quintana, Brucella melitensis, Burkholderia mallei, Burkholderia pseudomallei, Chlamydia psittaci, Clostridium botulinum, Clostridium perfringens, Coxiella bumetti*, enterohemorrhagic *Escherichia coli, Francisella tularensis, Rickettsia mooseri, Rickettsia prowasecki, Rickettsia rickettsii, Rickettsia tsutsugamushii, Salmonella typhi, Salmonella, Shigella, Shigella dysenteriae, Vibrio cholerae, Yersinia pestis, Coccidioides immitis, Histoplasma capsulatum*, chikungunya virus, Congo-Crimean haemorrhagic fever virus, dengue fever virus, Eastern equine encephalitis virus, ebola virus, equine morbillivirus, hantaan virus, Japanese encephalitis virus, junin virus, lassa fever virus, Epstein Barr virus (infectious mononucleosis), lymphocytic choriomeningitis virus, machupo virus, marburg virus, monkey pox virus, Murray valley encephalitis virus, nipah virus, Omsk hemorrhagic fever virus, oropouche virus, Rift valley fever virus, Russian Spring-Summer encephalitis virus, smallpox virus, South American hemorrhagic fever viruses, St. Louis encephalitis virus, tick-borne encephalitis virus. Variola virus, Venezuelan equine encephalitis virus, Western equine encephalitis virus, white pox virus, yellow fever virus, botulinum toxins, *Clostridium perfringens* toxins, microcystins (Cyanginosins), Shiga toxin, verotoxin, Staphylococcal enterotoxin B, anatoxin A, conotoxins, palytoxin, saxitoxin, tetrodotoxin, stachybotrys toxins, aflatoxins, trichothecenes, satratoxin H, T-2 toxin, and ricin. Other examples include *Abrus precatorius* lectin, African swine fever virus, avian influenza virus, banana bunchy top virus, bluetongue virus, camelpox virus, cholera toxin, *Clostridium perfringens, Clostridium tetani, Cryptosporidium parvum, Deuterophoma tracheiphila, Entamoeba histolytica*, ergot alkaloids, *Escherichia coli* 0157, foot and mouth disease virus, *Giardia, Giardia lamblia*, goat pox virus, hendra virus, hepatitis A virus, hog cholera virus, human immunodeficiency virus, infectious conjunctivitis virus, influenza virus (including influenza A, influenza B, and influenza C viruses), Kyasanur Forest virus, *Legionella pneumophila*, louping ill virus, lyssaviruses, *Adenia digitata* lectin (modeccin), *Monilia rorei, Naegleria fowleri*, nipah virus, Murray Valley encephalitis virus, *Mycoplasma mycoides*, newcastle disease virus, oropouche virus, peste des petits ruminants virus, porcine enterovirus 9, powassan virus, pseudorabies virus, rinderpest virus, rocio virus, group B rotaviruses, *Salmonella paratyphi*, sheeppox virus, St. Louis encephalitis virus, substance P, *Serratia marcescens*, Teschen-Talfan virus, tetanus toxin, vesicular stomatitis virus, *Visctim album* lectin 1 (Viscumin), *Adena volkensii* lectin (volkensin), West Nile virus, *Xanthomonas campestris* oryzae, *Xylella fastidiosa*, and *Yersinia pseudotuberculosis*.

In another embodiment, the systems and methods of the present disclosure can be used to assess pathogens including at least influenza A, influenza B, Group A Streptococcus, methicillin-resistant Staphylococcus aureus, Epstein Barr virus.

Exemplary plant pathogens include at least *Burkholderia solanacearum*, citrus greening disease bacteria, *Erwinia amylovora, Xanthomonas albilineans, Xanthomonas axonopodis* pv. *citri, Bipolaris* (Helminthosporium) *maydis, Claviceps purpurea, Colletotrichum coffeanum virulans, Cochliobolus miyabeanus, Dothistroma pini, Fusarium oxysporum, Microcystis ulei, Neovossia indica, Peronospora hyoscyami, Puccinia erianthi, Puccinia graminis, Puccinia graminis* f. sp. *tritici, Puccinia striiformis, Pyricularia grisea, Sclerotinia sclerotiorum, Sclerotium rolfsii, Tilletia indica, Ustilago maydis, Phytophthora infestans*, and Fiji disease virus.

Figure 5A:
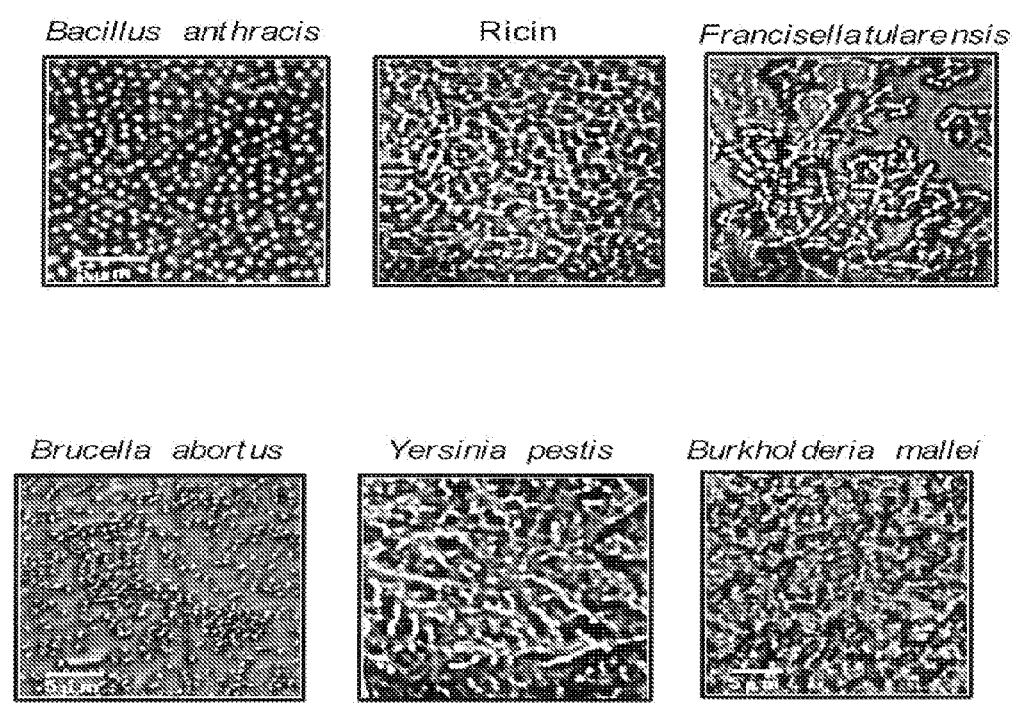
Figure 5B:
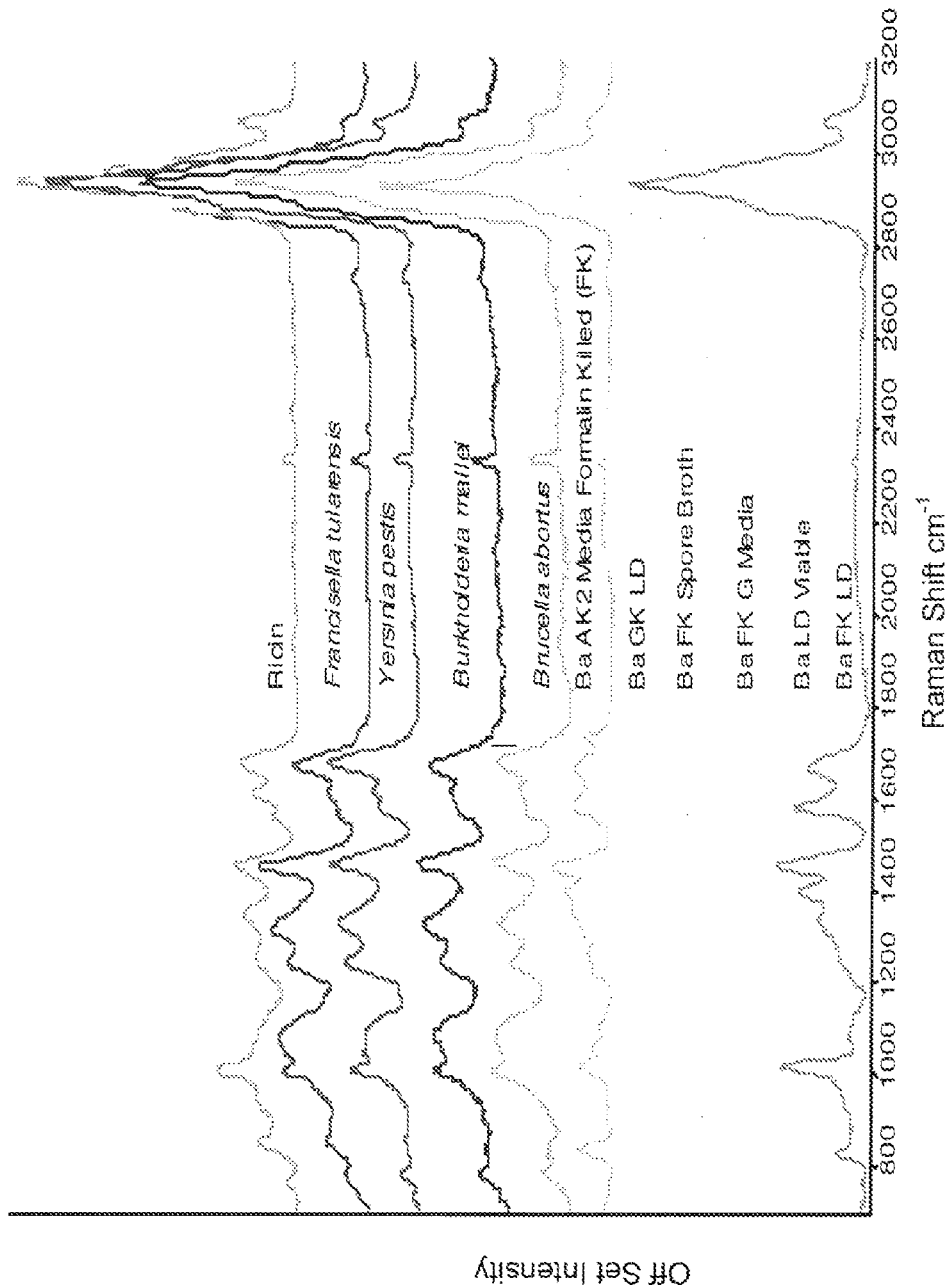
Figure 5C:
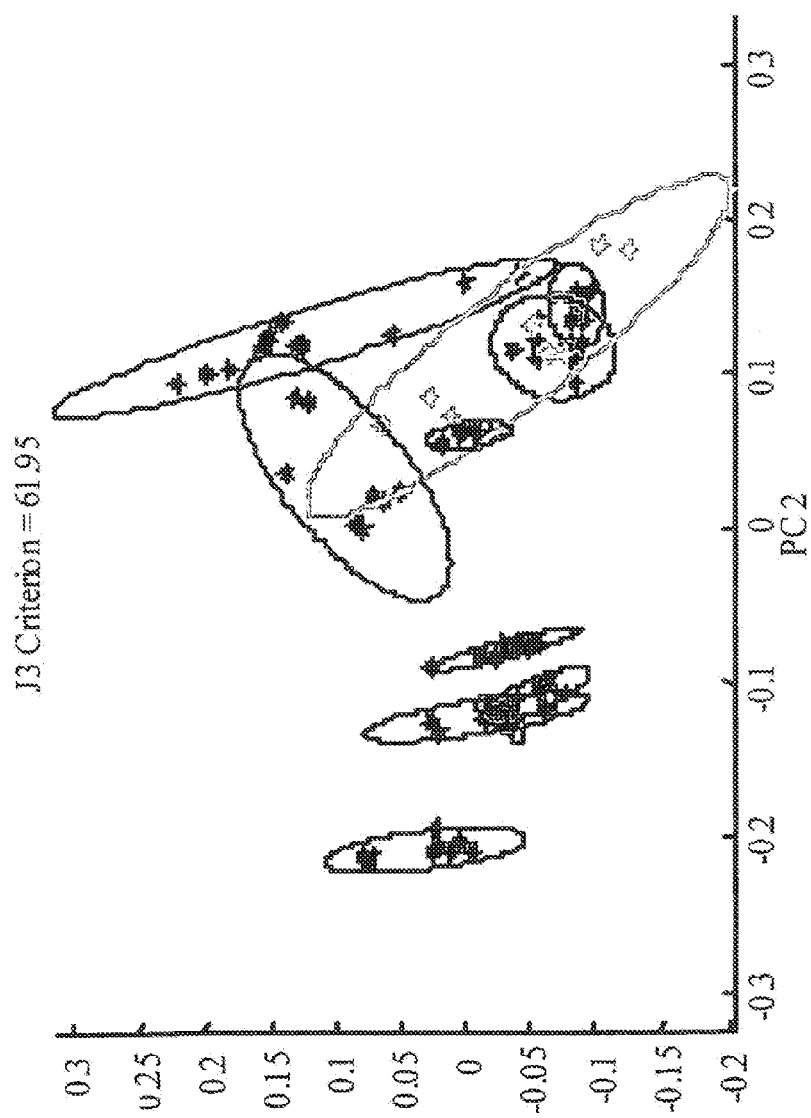
Figure 5D:
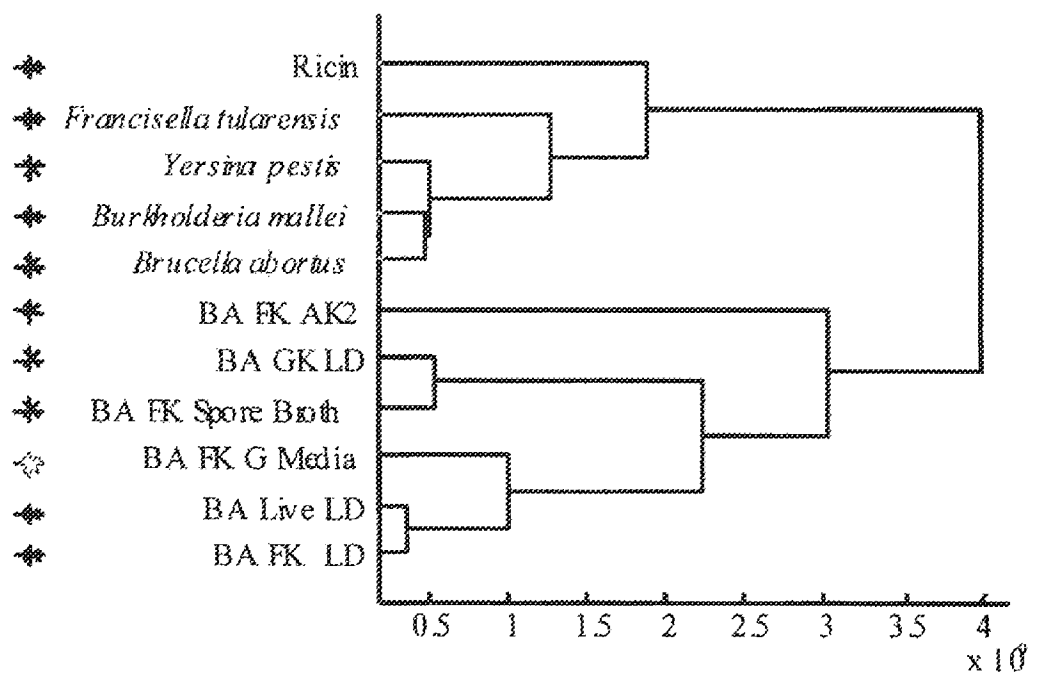
Figure 6:
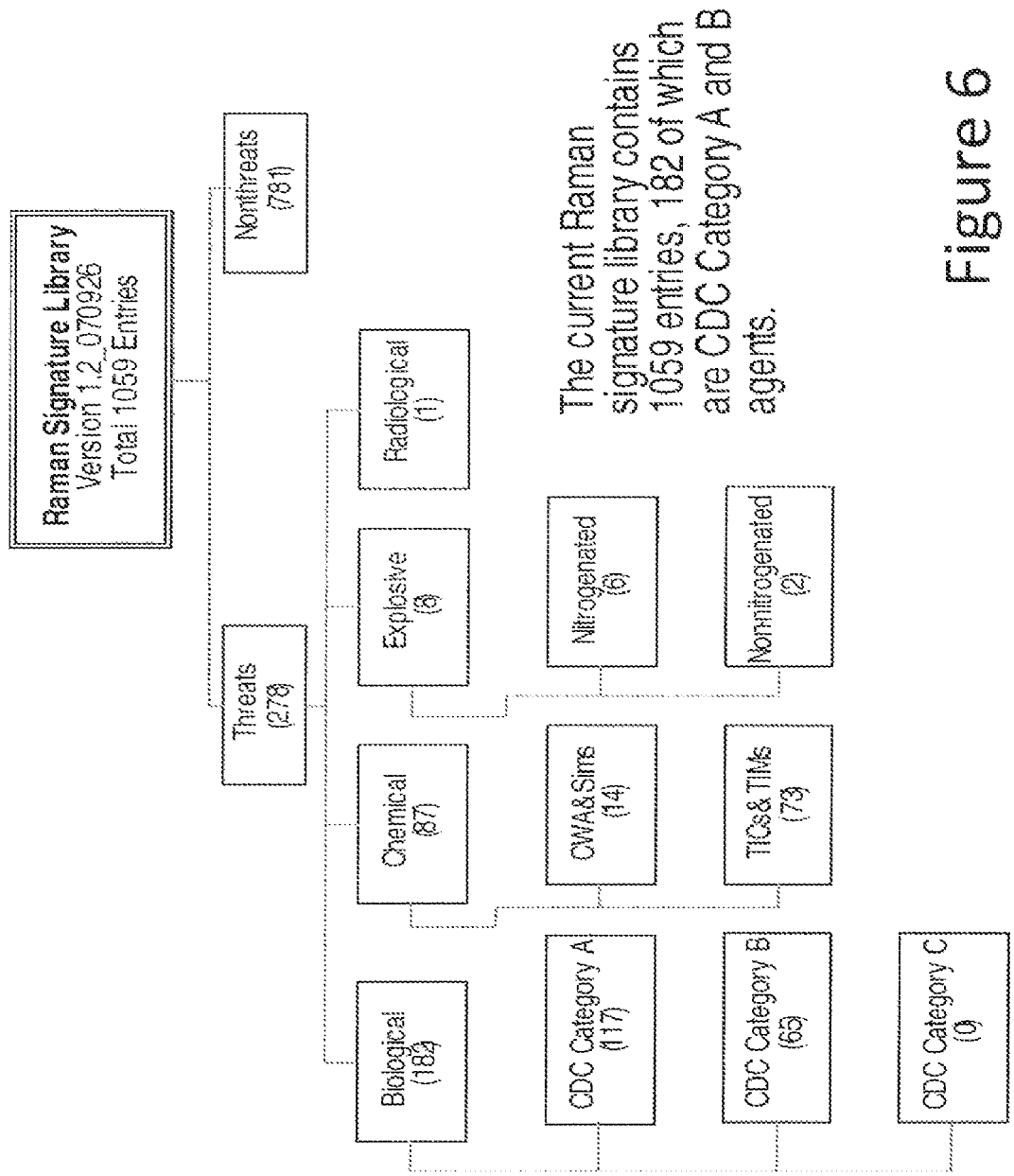
Figure 8:
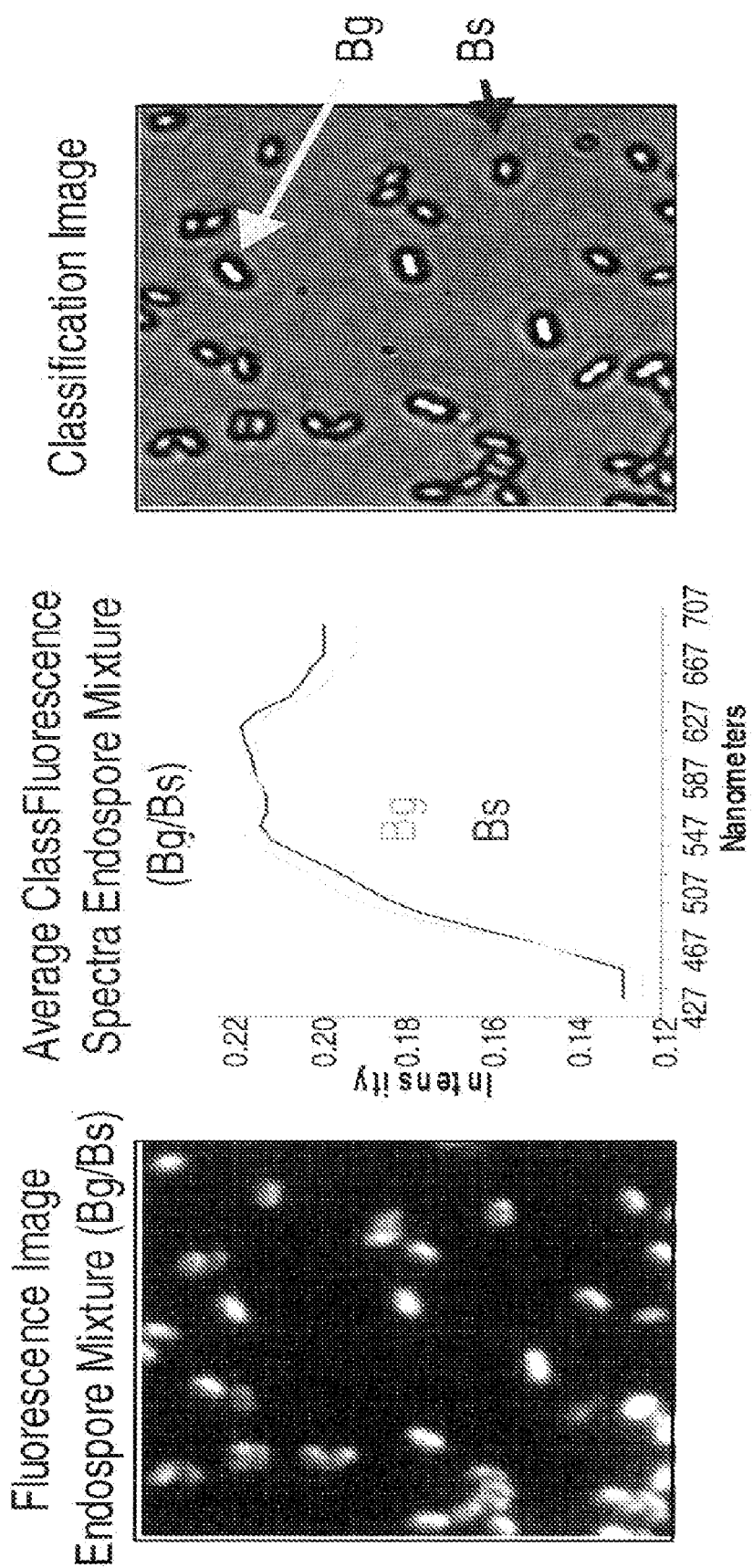
Figure 9:
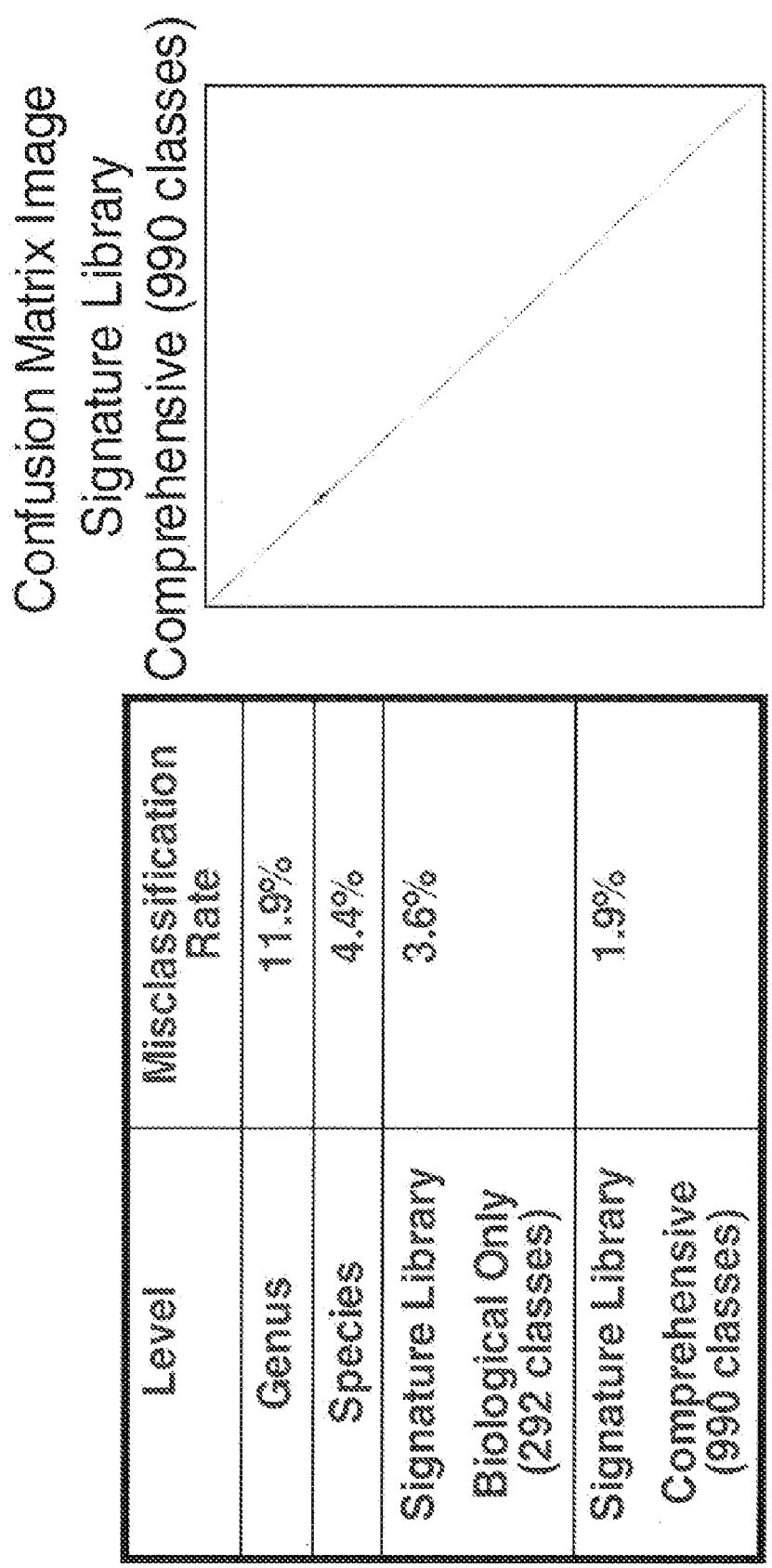

FIGS. 5A-5D illustrate the ability to discriminate and identify major bacteria of concern on the CDC category A and B list of pathogens as well as the toxin ricin. These materials include six different strains of *Bacillus anthracis* spores (BA FK AK2, BA GK LD, BAFK Spore Broth, BA FK G Media, BA Live LD, BA FK LD), Ricin, *Francisela tularensis, Brucella abortus, Yersinia pestis*, and *Burkholderia mallei*. In FIG. 5A, the bright field images of the materials on a slide are shown. The Raman spectra of the individual samples are shown in FIG. 5B. Although the spectra are very similar, a Mahalanobis differential classification scheme was applied to the data and the resultant cluster analysis is shown in FIG. 5C. The *Bacillus anthracis* spores are all clustered together on the right of FIG. 5C but are differentiable. For clarification, these have been labeled as follows: BA FK AK2 as 738, BA GK LD as 736, BA FK Spore Broth as 735, BA FK G Media as 740, BA Live LD as 739, BA FK LD as 737. Still referring to FIG. 5C, *Francisella tularensis*, 730, is the most removed on the far left of FIG. 5C and is always identifiable from the other biologicals. This is probably due to the higher fatty acid content of the material. The ricin toxin, 734, is separated from the other biological and the *Brucella abortus* 732, *Burkholderia mallei* 731, and *Yersinia pestis* 733 are close together in the middle, but individually identifiable. A dendogram showing the linkage of the materials is represented in FIG. 5D. All of the materials are related by the Raman data, as we would expect them to be from the biological tree.

A biological repository that encompasses the CDC Category A and B (182 entries) list as well as thousands of other biological organisms may be available for testing. In one embodiment, the Raman signature database contains approximately 1,059 signatures, 358 of which are comprised of biological materials (both threat and non-threat) from AFIP (Armed Forces Institute of Pathology). A breakdown of the Raman signature library is shown in FIG. 6. Other items classified as non-threats include pharmaceuticals, polymers, and consumer products.

In one embodiment, organisms are maintained in the AFIP repository in cryovials. Samples are subbed out from the thawed cryovials onto organism-appropriate agar plates and incubated overnight. A single colony is taken from the plate and an organism appropriate broth is inoculated. Broth flasks are left in a heated shaker until desired turbidity (organism growth) is achieved. Samples are washed down from the broth until slide preps indicate that growth debris has been sufficiently removed. Sample purity is checked with purity plates, particle sizing, and biochemical tests. The samples are deposited on aluminum-coated microscope slides. In one embodiment, Raman spectra can be obtained from ten (10) regions of interest using the FALCON™ Raman Chemical Imaging Microscope. Collecting multiple spectra per sample provides greater confidence in spectral classification and enables class-based library searches rather than single point searches. The data generated (spectra and digital images) is then entered into the Raman signature database.

Infrared absorption spectroscopy (IR) offers a rapid spectral fingerprint identification of microorganisms with minimal sample preparation without the use of reagents. It is highly differential to subspecies and due to these capabilities IR can be used to monitor microbial growth changes. IR provides whole organism fingerprinting and is uniformly applicable to all microorganisms. Combining IR with other spectroscopic techniques broadens the capability of any one data set. Multivariate statistical analysis and pattern recognition techniques can be used to elucidate the multi-dimensionality of the hyperspectral data sets. FIG. 7 illustrates how IR is used to distinguish between two *Bacillus* species, *Bacillus anthracis* and *Bacillus globigii*. This data, collected at AFIP with ChemID FTIR-ATR technology from Smiths Detection, is differentiable in the fingerprint region (700-1800 $cm^{-1}$). Specific differences are seen at approximately 1300 $cm^{-1}$.

Fluorescence imaging microscopy is a standard tool in both medical and biological research. Fluorescence occurs when a photon is absorbed resulting in the emission of a photon with a longer wavelength. Emission profiles are generally broad and have a tendency to overlap. However, it has been demonstrated that some discrimination is possible. FIG. 8 shows how fluorescence imaging may be used to discriminate *Bacillus globigii* from *Bacillus stereothermopilus* using both morphology and spectroscopy. The spatial/spectral classifier provides improved performance over morphology-only or fluorescence-only classifiers operating independently. While this methodology is not anticipated to provide robust, species-level identification, it is anticipated to be suitable for spore or vegetative cell vs. non-biological technique alone may not be able to identify specific threats, it has the potential to increase identification when fused with Raman and infrared spectroscopy.

Another aspect of developing a spectral signature database is database validation. In one embodiment, an extensive validation protocol is developed to verify existing data was compliant. These tests included a thorough review of all existing entries for baseline fit, signal-to-noise ratio and instrument response corrections. Non-compliant data was eliminated entirely, re-corrected or re-collected. In addition to this evaluation, both an inter-laboratory study and a cross platform validation study were conducted at laboratories at AFIP and ChemImage. In both studies, a variety of samples including standards (e.g. acetaminophen) and biological samples (e.g. *bacillus globigii*) were analyzed. The results proved that Raman signatures collected in different laboratories, on a variety of laboratory sensors, by a number of operators can be used for species level identification, including discrimination among genetic near-neighbors. Additional validation steps included a controlled study to measure variance, measurement of spectral library searching accuracy and precision, and assessment of the identification performance of the library.

A step in assessing the performance of the database was to determine the degree of specificity achievable using Raman as a detection phenomenology. In order to support this validation, a taxonomy has been developed for structuring the Raman signature library. Discrimination performance had been assessed at the following levels: (1) Genus level; (2) Species level; and (3) Signature Library Entry Level, including (3A) evaluation of all bioagent entries and (3B) a comprehensive, library-wide evaluation of most library entries (i.e., 990). The results can be seen in FIG. 9 along with an image representing the confusion matrix for the comprehensive signature library, which had a misclassification rate of 1.9%. The discrimination performance was assessed using a defined algorithm and a consistent set of metrics. Specifically, the library was subset into various classes specific to a given test, followed by Raman signature classification using a supervised Mahalanobis distance classifier. The results of these analyses may be visualized as well.

Prior to the data collection proposed herein, a thorough gap analysis (of existing Raman, fluorescence, and IR databases) with more advanced validation steps may be performed. The currently existing set of spectra data may be reviewed and the gaps that are identified may serve as the roadmap for additional data collections.

Another step in improving the quality of the database is to further improve data collection efficiency and throughput, by upgrading the current Raman system with FAST technology (Fiber Array Spectral Translator). The heart of the FAST system is the fiber bundle. One end of the bundle collects the Raman scattered light from the collection optics and the other provides a linear array of fibers centered on the spectrometer slit. An upgrade may increase the current 7-fiber bundle to 19. This increase may also enable the user to collect 19 spatially resolved spectra at once to further expand the database.

An emerging technology in the field of spectroscopic imaging is the use of fiber optic arrays. We have termed this technology Fiber Array Spectral Translators (FAST) but it is also described as dimension reduction arrays. FAST technology can acquire a few to thousands of full spectral range, spatially resolved spectra simultaneously. This is done by focusing a spectroscopic image onto a two dimensional array of optical fibers that are drawn into a one-dimensional distal array with serpentine ordering. The one dimensional fiber stack is coupled to an imaging spectrograph. Software then extracts the spectral/spatial information that is embedded in a single CCD image frame. Fiber array spectroscopic imaging has been demonstrated in several applications including Raman chemical imaging analysis of micro-composites and biomaterials and time-resolved atomic emission chemical imaging of laser-induced plumes.

The fundamental advantage of this method over other spectroscopic imaging methods is speed of analysis. A complete spectroscopic imaging data set can be acquired in the amount of time it takes to generate a single spectrum from a given material. A current limitation of FAST is the low image definition (number of image pixels) in the object field. Image definition is dictated by the number of elements in the long axis direction of the detector. Alternatives to current designs can include the use of multiple detectors, which has the potential to increase the image definition. Even with limited pixel definition, superimposing color-coded spectroscopic images on high-spatial resolution gray-scale images can provide significant insight into the morphology and chemistry of materials.

The complementary information from the multiple techniques may provide better spectral discrimination than the reliance on a single spectroscopic technique. The algorithms used to combine multiple sources of complementary data fall under the category of data fusion. ChemImage's Forensics Integrated Search Technology (FIST) allows spectral searches of multiple spectroscopic sources of data. In one embodiment, the data fusion method is Bayesian fusion. The spectroscopic approaches are conducted independently. Each search results in a set of scores with one score for each member in the library—either an individual sample or a class with multiple spectra. The scores represent a distribution of numbers and can be converted to probabilities by converting to Z scores and using the Gaussian distribution probability table.

The results show that one can obtain much better discrimination using multiple spectroscopic techniques rather than just one spectroscopic technique. FIG. 10 shows the results of performing a spectral search for mid-Infrared, EDS, and Raman spectra of 27 commercial products. It can be seen that the FIST database can produce database search results that are better than the individual technique. Using all three techniques with data fusion gives results that are 450 to 550% better than any individual technique and using any two of the three techniques gives results that are 250 to 450% better than any individual technique. These results prove that data fusion may increase one's ability to correctly identify unknowns when using a database comprised of three sensors fused.

A substantial Raman signature spectral library database that includes many CDC Category A and B agents can be developed. The database can be constructed using multivariate statistical tools to build class-based models rather than single sample based spectral searches.

A library of known threat agent spectral profiles against Category A and B or the CDC list of bioterrorism agents may also be developed. The development of this database is relevant to the goal of the identification of pathogens involved with human infections. Spectroscopic tools are reagentless methods to detect a broad range of pathogens and hazardous chemicals. The development of this signature database and, in particular, the development of sensor fusion tools to utilize this database may greatly enhance the ability to identify hazards in the clinical as well as field environments.

FIST utilizes a relational database that stores textual and spectral data of known commercial products and allows advanced searching. A multi-data type search method using a Bayesian data fusion algorithm was implemented, combining individual search results from multiple data sources (Raman and FTIP, as well as chemical and physical property textual searches). The user will be able to set weighting factors and interactively view search results of both the overall and individual searches. FIST is a scalable solution that surpassed current technologies in its ability to be automated, handle mixture samples, and offer estimates of predictive performance.

The sensor fusion-based database helps characterize contaminants found within the products. It may be configured to search only text fields (such as color, FTIR type, energy dispersive (X-ray) spectrometry (EDS) components, microscopic description etc.), but may also contain digital images, FTIR spectra, and EDS information associated with every entry.

The generated Raman signature database (RCIBD) follows guidelines for creating a database product. A database product consists of the set of spectral data for which the chemical/biological identifications are known, a set of algorithms that allow spectral searching of the database in a manner that is accurate and specific, and a commercial software package that allows the user to access the data. This discussion addresses each of these aspects.

There are a number of companies that produce spectral library packages. Spectral library database products have a standard set of requirements that must be met including, but not limited to, the ability for users to setup customizable settings, perform database management, and add to the data database. In addition, there are standard processes by which commercial software is developed—such as the IEEE 12207 standard for the Software Development Life Cycle.

Standard spectral library packages may not provide the highly specific spectral data that has been collected to date by AFIP. Furthermore, standard spectral library packages may not provide the advanced searching capabilities that are provided by ChemImage. Standard spectral library search packages provide one spectrum per library material (sample). When a spectral search is performed, the target spectrum is compared to each library spectrum in the database. On the other hand, the present disclosure relates to using multiple spectra per sample, which allows the usage of class-based searches in which the target spectrum is compared to sets of spectra that represent samples rather than a single spectrum per sample. The sets of spectra are generally referred to as classes. The use of data fusion is another advanced searching capability that may also be implemented.

EXAMPLES

Example 1

In this example, a network of n spectroscopic instruments each provide test data sets to a central processing unit. Each instrument makes an observation vector $\{Z\}$ of parameter $\{X\}$. For instance, a dispersive Raman spectrum would be modeled with X=dispersive Raman and Z=the spectral data. Each instrument generates a test data set and calculates (using a similarity metric) the likelihoods $\{p_i(H_a)\}$ of the test data set being of type $H_a$. Bayes' theorem gives:

$$p(H_a | \{Z\}) = \frac{p(\{Z\} | H_a) p(H_a)}{p(\{Z\})} \quad \text{(Equation 1)}$$

where:
$p(H_a|\{Z\})$: the posterior probability of the test data being of type $H_a$, given the observations $\{Z\}$;
$p(\{Z\}|H_a)$: the probability that observations $\{Z\}$ were taken, given that the test data is type $H_a$;
$p(H_a)$: the prior probability of type $H_a$ being correct; and
$p(\{Z\})$: a normalization factor to ensure the posterior probabilities sum to 1.

Assuming that each spectroscopic instrument is independent of the other spectroscopic instruments gives:

$$p(\{Z\} \mid H_a) = \prod_{i=1}^{n} p_i(\{Z_i\} \mid H_a) \quad \text{(Equation 2)}$$

and from Bayes rule $$p(\{Z\} \mid H_a) = \prod_{i=1}^{n} (p_i(\{Z_i\} \mid \{X\}) p_i(\{X\} \mid H_a) \quad \text{(Equation 3)}$$

gives $$p(H_a \mid \{Z\}) = \alpha \cdot p(H_a) \prod_{i=1}^{n} [(p_i(\{Z_i\} \mid \{X\}) p_i(\{X\} \mid H_a)] \quad \text{(Equation 4)}$$

Equation 4 is the central equation that uses Bayesian data fusion to combine observations from different spectroscopic instruments to give probabilities of the presumed identities.

To infer a presumed identity from the above equation, a value of identity is assigned to the test data having the most probable (maximum a posteriori) result:

$$\hat{H}_a = \arg\max_a p(H_a \mid \{Z\}) \quad \text{(Equation 5)}$$

To use the above formulation, the test data is converted to probabilities. In particular, the spectroscopic instrument must give $p(\{Z\} \mid H_a)$, the probability that observations $\{Z\}$ were taken, given that the test data is type $H_a$. Each sublibrary is a set of reference data sets that match the test data set with certain probabilities. The probabilities of the unknown matching each of the reference data sets must sum to 1. The sublibrary is considered as a probability distribution.

The system applies a few commonly used similarity metrics consistent with the requirements of this algorithm: Euclidean Distance, the Spectral Angle Mapper (SAM), the Spectral Information Divergence (SID), Mahalanobis distance metric and spectral unmixing. The SID has roots in probability theory and is thus the best choice for the use in the data fusion algorithm, although either choice will be technically compatible. Euclidean Distance ("ED") is used to give the distance between spectrum x and spectrum y:

$$ED(x, y) = \sqrt{\sum_{i=1}^{L} (x_i - y_i)^2} \quad \text{(Equation 6)}$$

Spectral Angle Mapper ("SAM") finds the angle between spectrum x and spectrum y:

$$SAM(x, y) = \cos^{-1}\left(\frac{\sum_{i=1}^{L} x_i y_i}{\sqrt{\sum_{i=1}^{L} x_i^2} \sqrt{\sum_{i=1}^{L} y_i^2}}\right) \quad \text{(Equation 7)}$$

When SAM is small, it is nearly the same as ED. Spectral Information Divergence ("SID") takes an information theory approach to similarity and transforms the x and y spectra into probability distributions p and q:

$$p = [p_1, p_2, \ldots, p_L]^T, \quad q = [q_1, q_2, \ldots, q_L]^T \quad \text{(Equation 8)}$$

$$p_i = \frac{x_i}{\sum_{i=1}^{L} x_i}, \quad q_i = \frac{y_i}{\sum_{i=1}^{L} y_i}$$

The discrepancy in the self-information of each band is defined as:

$$D_i(x_i \parallel y_i) = \log\left[\frac{p_i}{q_i}\right] \quad \text{(Equation 9)}$$

So the average discrepancies of x compared to y and y compared to x (which are different) are:

$$D(x \parallel y) = \sum_{i=1}^{L} p_i \log\left[\frac{p_i}{q_i}\right], \quad D(y \parallel x) = \sum_{i=1}^{L} q_i \log\left[\frac{q_i}{p_i}\right] \quad \text{(Equation 10)}$$

The SID is thus defined as:

$$SID(x,y) = D(x \parallel y) + D(y \parallel x) \quad \text{(Equation 11)}$$

A measure of the probabilities of matching a test data set with each entry in the sublibrary is needed. Generalizing a similarity metric as m(x, y), the relative spectral discrimination probabilities is determined by comparing a test data set x against k library entries.

$$p_{x,Library}(k) = 1 - \frac{m(x, y_k)}{\sum_{i=1}^{L} m(x, y_i)} \quad \text{(Equation 12)}$$

Equation 12 is used as $p(\{Z\} \mid H_a)$ for each sensor in the fusion formula.

Assuming, a library consists of three reference data sets: $\{H\} = \{A, B, C\}$. Three spectroscopic instruments (each a different modality) are applied to this sample and compare the outputs of each spectroscopic instrument to the appropriate sublibraries (i.e. dispersive Raman spectrum compared with library of dispersive Raman spectra). If the individual search results, using SID, are:

$$SID(x_{Raman}, Library_{Raman}) = \{20, 10, 25\}$$

$$SID(x_{Fluor}, Library_{Fluor}) = \{40, 35, 50\}$$

$$SID(x_{IR}, Library_{IR}) = \{50, 20, 40\}$$

Applying Equation 12, the relative probabilities are:

$$p(Z_{\{Raman\}} \mid \{H\}) = \{0.63, 0.81, 0.55\}$$

$$p(Z_{\{Fluor\}} \mid \{H\}) = \{0.68, 0.72, 0.6\}$$

$$p(Z_{\{IR\}} \mid \{H\}) = \{0.55, 0.81, 0.63\}$$

It is assumed that each of the reference data sets is equally likely, with:

$$p(\{H\}) = \{p(H_A), p(H_B), p(H_C)\} = \{0.33, 0.33, 0.33\}$$

Applying Equation 4 results in:

$$p(\{H\} \mid \{Z\}) = \square \times \{0.33, 0.33, 0.33\} \times [\{0.63, 0.81, 0.55\} \cdot \{0.68, 0.72, 0.6\} \cdot \{0.55, 0.81, 0.63\}]$$

$$p(\{H\} \mid \{Z\}) = \square \times \{0.0779, 0.1591, 0.0687\}$$

Now normalizing with $\square \square 1/(0.0779 + 0.1591 + 0.0687)$ results in:

$$p(\{H\} \mid \{Z\}) = \{0.25, 0.52, 0.22\}$$

The search identifies the unknown sample as reference data set B, with an associated probability of 52%.

Example 2

Raman and mid-infrared sublibraries each having reference data set for 61 substances were used. For each of the 61 substances, the Raman and mid-infrared sublibraries were searched using the Euclidean distance vector comparison. In other words, each substance is used sequentially as a target vector. The resulting set of scores for each sublibrary were converted to a set of probability values by first converting the score to a Z value and then looking up the probability from a Normal Distribution probability table. The process was repeated for each spectroscopic technique for each substance and the resulting probabilities were calculated. The set of final probability values was obtained by multiplying the two sets of probability values.

The results are displayed in Table 1. Based on the calculated probabilities, the top match (the score with the highest probability) was determined for each spectroscopic technique individually and for the combined probabilities. A value of "1" indicates that the target vector successfully found itself while a value of "0" indicates that the target vector found some match other than itself as the top match. The Raman probabilities resulted in four incorrect results, the mid-infrared probabilities resulted in two incorrect results, and the combined probabilities resulted in no incorrect results.

The more significant result is the fact that the distance between the top match and the second match is significantly large for the combined approach as opposed to Raman or mid-infrared for almost all of the 61 substances. In fact, 15 of the combined results have a difference that is a four times greater distance than the distance for either MIR or Raman, individually. Only five of the 61 substances do not benefit from the fusion algorithm.

| Index | Substance | Raman | MIR | Combined | Raman Distance | MIR Distance | Combined Distance |
|---|---|---|---|---|---|---|---|
| 1 | 2-Propanol | 1 | 1 | 1 | 0.0429 | 0.0073 | 0.0535 |
| 2 | Acetamidophenol | 1 | 1 | 1 | 0.0406 | 0.0151 | 0.2864 |
| 3 | Acetone | 1 | 1 | 1 | 0.0805 | 0.0130 | 0.2294 |
| 4 | Acetonitrile | 1 | 1 | 1 | 0.0889 | 0.0167 | 0.4087 |
| 5 | Acetylsalicylic Acid | 1 | 1 | 1 | 0.0152 | 0.0152 | 0.0301 |
| 6 | Ammonium Nitrate | 0 | 1 | 1 | 0.0000 | 0.0467 | 0.0683 |
| 7 | Benzalkonium Chloride | 1 | 1 | 1 | 0.0358 | 0.0511 | 0.1070 |
| 8 | Caffeine | 1 | 1 | 1 | 0.0567 | 0.0356 | 0.1852 |
| 9 | Calcium Carbonate | 1 | 1 | 1 | 0.0001 | 0.0046 | 0.0047 |
| 10 | Calcium chloride | 1 | 1 | 1 | 0.0187 | 0.0076 | 0.2716 |
| 11 | Calcium Hydroxide | 1 | 1 | 1 | 0.0009 | 0.0006 | 0.0015 |
| 12 | Calcium Oxide | 1 | 1 | 1 | 0.0016 | 0.0848 | 0.1172 |
| 13 | Calcium Sulfate | 0 | 1 | 1 | 0.0000 | 0.0078 | 0.2818 |
| 14 | Cane Sugar | 1 | 1 | 1 | 0.0133 | 0.0006 | 0.0137 |
| 15 | Charcoal | 1 | 1 | 1 | 0.0474 | 0.0408 | 0.1252 |
| 16 | Cocaine_pure | 1 | 1 | 1 | 0.0791 | 0.0739 | 0.2261 |
| 17 | Creatine | 1 | 1 | 1 | 0.1102 | 0.0331 | 0.3751 |
| 18 | D-Fructose | 1 | 1 | 1 | 0.0708 | 0.0536 | 0.1336 |
| 19 | D-Amphetamine | 1 | 0 | 1 | 0.0400 | 0.0000 | 0.0400 |
| 20 | Dextromethorphan | 1 | 1 | 1 | 0.0269 | 0.1067 | 0.2940 |
| 21 | Dimethyl Sulfoxide | 1 | 1 | 1 | 0.0069 | 0.0466 | 0.1323 |
| 22 | D-Ribose | 1 | 1 | 1 | 0.0550 | 0.0390 | 0.1314 |
| 23 | D-Xylose | 1 | 1 | 1 | 0.0499 | 0.0296 | 0.1193 |
| 24 | Ephedrine | 1 | 1 | 1 | 0.0367 | 0.0567 | 0.2067 |
| 25 | Ethanol_processed | 1 | 1 | 1 | 0.0269 | 0.0276 | 0.1574 |
| 26 | Ethylene Glycol | 1 | 1 | 1 | 0.1020 | 0.0165 | 0.1692 |
| 27 | Ethylenediamine-tetraacetate | 1 | 1 | 1 | 0.0543 | 0.0312 | 0.2108 |
| 28 | Formula 409 | 1 | 1 | 1 | 0.0237 | 0.0063 | 0.0663 |
| 29 | Glycerol GR | 1 | 1 | 1 | 0.0209 | 0.0257 | 0.1226 |
| 30 | Heroin | 1 | 1 | 1 | 0.0444 | 0.0241 | 0.2367 |
| 31 | Ibuprofen | 1 | 1 | 1 | 0.0716 | 0.0452 | 0.2785 |
| 32 | Ketamine | 1 | 1 | 1 | 0.0753 | 0.0385 | 0.2954 |
| 33 | Lactose Monohydrate | 1 | 1 | 1 | 0.0021 | 0.0081 | 0.0098 |
| 34 | Lactose | 1 | 1 | 1 | 0.0021 | 0.0074 | 0.0092 |
| 35 | L-Amphetamine | 1 | 0 | 1 | 0.0217 | 0.0000 | 0.0217 |
| 36 | Lidocaine | 1 | 1 | 1 | 0.0379 | 0.0418 | 0.3417 |
| 37 | Mannitol | 1 | 1 | 1 | 0.0414 | 0.0361 | 0.0751 |
| 38 | Methanol | 1 | 1 | 1 | 0.0996 | 0.0280 | 0.1683 |
| 39 | Methcathinone-HCl | 1 | 1 | 1 | 0.0267 | 0.0147 | 0.0984 |
| 40 | Para-methoxymethyl-amphetamine | 1 | 1 | 1 | 0.0521 | 0.0106 | 0.0689 |
| 41 | Phenobarbital | 1 | 1 | 1 | 0.0318 | 0.0573 | 0.1807 |
| 42 | Polyethylene Glycol | 1 | 1 | 1 | 0.0197 | 0.0018 | 0.1700 |
| 43 | Potassium Nitrate | 0 | 1 | 1 | 0.0000 | 0.0029 | 0.0125 |
| 44 | Quinine | 1 | 1 | 1 | 0.0948 | 0.0563 | 0.2145 |
| 45 | Salicylic Acid | 1 | 1 | 1 | 0.0085 | 0.0327 | 0.2111 |
| 46 | Sildenfil | 1 | 1 | 1 | 0.1049 | 0.0277 | 0.1406 |

-continued

| Index | Substance | Raman | MIR | Combined | Raman Distance | MIR Distance | Combined Distance |
|---|---|---|---|---|---|---|---|
| 47 | Sodium Borate Decahydrate | 1 | 1 | 1 | 0.0054 | 0.0568 | 0.0618 |
| 48 | Sodium Carbonate | 1 | 1 | 1 | 0.0001 | 0.0772 | 0.0915 |
| 49 | Sodium Sulfate | 1 | 1 | 1 | 0.0354 | 0.0023 | 0.3190 |
| 50 | Sodium Sulfite | 1 | 1 | 1 | 0.0129 | 0.0001 | 0.3655 |
| 51 | Sorbitol | 1 | 1 | 1 | 0.0550 | 0.0449 | 0.1178 |
| 52 | Splenda Sugar Substitute | 1 | 1 | 1 | 0.0057 | 0.0039 | 0.0093 |
| 53 | Strychnine | 1 | 1 | 1 | 0.0710 | 0.0660 | 0.2669 |
| 54 | Styrofoam | 1 | 1 | 1 | 0.0057 | 0.0036 | 0.0453 |
| 55 | Sucrose | 1 | 1 | 1 | 0.0125 | 0.0005 | 0.0128 |
| 56 | Sulfanilamide | 1 | 1 | 1 | 0.0547 | 0.0791 | 0.1330 |
| 57 | Sweet N Low | 1 | 1 | 1 | 0.0072 | 0.0080 | 0.0145 |
| 58 | Talc | 0 | 1 | 1 | 0.0000 | 0.0001 | 0.5381 |
| 59 | Tannic Acid | 1 | 1 | 1 | 0.0347 | 0.0659 | 0.0982 |
| 60 | Tide detergent | 1 | 1 | 1 | 0.0757 | 0.0078 | 0.2586 |
| 61 | Urea | 1 | 1 | 1 | 0.0001 | 0.0843 | 0.1892 |

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method comprising:
   a) providing a library having a plurality of sublibraries, wherein each said sublibrary contains a plurality of reference data sets generated by at least one of a corresponding one of a plurality of spectroscopic data generating instruments associated with said sublibrary, and wherein each reference data set characterizes a corresponding known pathogenic microorganism;
   b) obtaining a plurality of test data sets characteristic of an unknown material, wherein each test data set is generated by at least one of the plurality of spectroscopic data generating instruments;
   c) instructing a processor to perform the following:
      d) for each test data set, searching each sublibrary associated with the spectroscopic data generating instrument used to generate said test data set, to thereby produce a corresponding set of scores for each searched sublibrary, wherein each score in said set of scores indicates a likelihood of a match between a corresponding one of said plurality of reference data sets in said searched sublibrary and said test data set;
      e calculating a set of relative probability values for each searched sublibrary based on the corresponding set of scores for each searched sublibrary; and
      f fusing all relative probability values using Bayesian fusion to thereby produce a set of final probability values to be used in determining whether said unknown material is represented through a corresponding known pathogenic microorganism characterized in the library.

2. The method of claim 1 wherein said plurality of test data sets are obtained by:
   a) illuminating a sample containing said unknown material with substantially monochromatic light to thereby produce Raman scattered photons;
   b) illuminating said sample with broadband light to thereby produce scattered photons;
   c) receiving said Raman scattered photons and said scattered photons substantially simultaneously from a plurality of spatial locations of said sample using a fiber array spectral translator; and
   d) detecting said Raman scattered photons and said scattered photons and providing therefrom a plurality of spatially accurate wavelength resolved spectra of said sample.

3. The method of claim 1 wherein said plurality, of test data sets are obtained by:
   a) illuminating a sample containing said unknown material with substantially monochromatic light to thereby produce Raman scattered photons;
   b) illuminating said sample with broadband light to thereby produce scattered photons;
   c) receiving said Raman scattered photons and said scattered photons substantially simultaneously from a plurality of spatial locations of said sample; and
   d) detecting said Raman scattered photons and said scattered photons and providing therefrom a plurality of spatially accurate wavelength resolved spectra of said sample.

4. The method of claim 1 wherein said plurality of test data sets are obtained by:
   a) illuminating a sample to thereby produce scattered photons;
   b) receiving said scattered photons using a fiber array spectral translator; and
   c) detecting said scattered photons and providing therefrom a plurality of spatially accurate wavelength resolved spectra of said sample.

5. The method of claim 1 wherein said plurality of test data sets are obtained by:
   a) illuminating a sample to thereby produce scattered photons;
   b) receiving said scattered photons; and
   c) detecting said scattered photons and providing therefrom a plurality of spatially accurate wavelength resolved spectra of said sample.

6. The method of claim 2 further comprising obtaining a spatially accurate wavelength resolved image of said sample.

7. The method of claim 3 further comprising obtaining a spatially accurate wavelength resolved image of said sample.

8. The method of claim 4 further comprising obtaining a spatially accurate wavelength resolved image of said sample.

9. The method of claim 5 further comprising obtaining a spatially accurate wavelength resolved image of said sample.

10. The method of claim 1 further comprising applying a weighting factor to each set of relative probability values, to thereby produce a set of weighted probability values for each searched sublibrary.

11. The method of claim 1 wherein said spectroscopic data generating instrument comprises at least one of the following: a Raman spectrometer, an infrared spectrometer, an x-ray diffractometer, an energy dispersive x-ray analyzer, a mass spectrometer, a microscope, an image generating instrument, a chromatographic analyzer, a charge-coupled detector, and a fluorescence spectrometer.

12. The method of claim 1 wherein said test data comprises at least one of the following: a Raman spectrum characteristic of said unknown, a Raman image characteristic of said unknown, an infrared spectrum characteristic of said unknown, a fluorescence image characteristic of said unknown, a fluorescence spectrum characteristic of said unknown, an infrared spectrum characteristic of said unknown, an infrared image characteristic of said unknown, an x-ray diffraction pattern characteristic of said unknown, an energy dispersive x-ray spectrum characteristic of said unknown, and a mass spectrum characteristic of said unknown.

13. The method of claim 1 further comprising:
a) providing a text description of each known pathogenic microorganism represented in the plurality of sublibraries;
b) individually searching each sublibrary, using a text query, that compares the text query to the text description of each known pathogenic microorganism to thereby produce a match answer or no match answer for each known pathogenic microorganism; and
c) removing the reference data set, from each sublibrary, for each known pathogenic microorganism producing the no match answer.

14. The method of claim 1 further comprising:
a) providing an image sublibrary containing a plurality of reference images generated by an image generating instrument associated with said image sublibrary;
b) wherein each reference image characterizes a corresponding known pathogenic microorganism, obtaining an image test data set characterizing an unknown material, wherein the image test data set is generated by said image generating instrument;
c) comparing the image test data set to the plurality of reference images; and
d) in accordance with said comparing, producing a match answer or a no match answer for each known pathogenic microorganism.

15. The method of claim 1 further comprising: a) obtaining a spectra test data set characterizing an unknown material, wherein the spectra test data set is generated by said spectra generating instrument; b) comparing the spectra test data set to the plurality of reference spectra; and c) in accordance with said comparing, producing a match answer or a no match answer for each known pathogenic microorganism.

16. The method of claim 15, wherein for each known pathogenic microorganism producing a match answer, identifying one or more of the following: a strain of said known pathogenic microorganism and a species of said known pathogenic microorganism.

17. The method of claim 1, wherein said reference data set comprises a plurality of reference spectra.

18. The method of claim 17 wherein said plurality of reference data sets are generated by at least two different of the corresponding plurality of spectroscopic data generating instruments associated with said sublibrary.

19. The method of claim 1, wherein said reference data set comprises a plurality of reference spectra.

20. The method of claim 19, wherein said plurality of reference spectra are generated by one corresponding plurality of spectroscopic data generating instruments associated with said sublibrary.

21. The method of claim 1 wherein said fusion is achieved by Bayesian fusion.

22. The method of claim 1 wherein the pathogenic microorganism is selected from the group consisting of filoviruses, naviruses, alphaviruses, and combinations thereof.

23. The method of claim 1 wherein the pathogenic microorganism is selected from the group of microorganisms consisting of protozoa, cryptosporidia microorganisms, *Escherichia coli*, *Escherichia coli* 157 microorganisms, Plague (*Yersinia pestis*), Smallpox (variola major), *Tularemia* (*Francisella tularensis*), Brucellosis (*Brucella* species), *Clostridium perfringens, Salmonella, Shigella,* Glanders (*Burkholderia mallei*), Melioidosis (*Burkholderia pseudomallei*), Psittacosis (*Chlamydia psittaci*), Q fever (*Coxiella burnetii*), Typhus fever (*Rickettsia prowazekii*), *Vibrio cholerae*, and combinations thereof.

24. The method of claim 1 wherein the pathogenic microorganism is selected from the group of bacteria consisting of *Giardia, Candida albicans, Enterococcus faecalis, Staphylococcus epidermidis, Enterobacter aerogenes, Corynebacterium diphtheriae, Pseudomonas aeruginosa, Acinetobacter calcoaceticus, Klebsiella pneumoniae*, and *Serratia marcescens*, and combinations thereof.

25. The method of claim 1 wherein the pathogenic microorganism is selected from the group fungus consisting of *Microsporum audouini, Microspotum canis, Microsporum gypseum, Trichophyton mentagrophytes* var. *mentagrophytes, Trichophyton mentagrophytes* var. *interdigitale, Trichophyton rubrum, Trichophyton tonsurans, Trichophyton verrucosum*, and *Epidermophytum floccosum*, and combinations thereof.

26. The method of claim 1 wherein the pathogenic microorganism is selected from the group consisting of: influenza A, influenza B, Epstein Barr virus, Group A streptococcus, Group B streptococcus, and combinations thereof.

27. The method of claim 1 wherein the pathogenic microorganism is *Staphylococcus aureus*.

28. The method of claim 1 wherein the pathogenic microorganism is methicillin-resistant *Staphylococcus aureus*.

29. The method of claim 1 further comprising analyzing patterns characteristic of the pathogenic microorganism to determine viability of the pathogenic microorganism.

* * * * *